US006360126B1

United States Patent
Mika et al.

(10) Patent No.: US 6,360,126 B1
(45) Date of Patent: Mar. 19, 2002

(54) APPARATUS AND METHOD FOR CONTROLLING THE DELIVERY OF CONTRACTILITY MODULATING NON-EXCITATORY SIGNALS TO THE HEART

(75) Inventors: Yuval Mika, Zichron-Yaacov (IL); David Prutchi, Lake Jackson, TX (US)

(73) Assignee: Impulse Dynamics N.V., Curacao (AN)

( * ) Notice: Subject to any disclaimer, the term of this patent is extended or adjusted under 35 U.S.C. 154(b) by 0 days.

(21) Appl. No.: 09/378,776

(22) Filed: Aug. 20, 1999

(51) Int. Cl.⁷ ................................................ A61N 1/362
(52) U.S. Cl. ............................................. 607/9; 607/17
(58) Field of Search ............................... 607/4, 5, 9, 17

(56) References Cited

U.S. PATENT DOCUMENTS

| | | | |
|---|---|---|---|
| 4,554,922 A | | 11/1985 | Prystowsky et al. |
| 4,559,947 A | | 12/1985 | Renger et al. |
| 4,971,058 A | | 11/1990 | Pless et al. |
| 5,083,564 A | | 1/1992 | Scherlag |
| 5,154,501 A | | 10/1992 | Svenson et al. |
| 5,172,699 A | | 12/1992 | Svenson et al. |
| 5,184,620 A | | 2/1993 | Cudahy et al. |
| 5,281,219 A | | 1/1994 | Kallok |
| 5,443,489 A | | 8/1995 | Ben-Haim |
| 5,447,520 A | * | 9/1995 | Spano et al. ............... 607/5 |
| 5,549,646 A | | 8/1996 | Katz et al. |
| 5,601,609 A | * | 2/1997 | Duncan ..................... 607/5 |
| 5,871,506 A | | 2/1999 | Mower |
| 6,152,882 A | * | 11/2000 | Prutchi ...................... 600/509 |

FOREIGN PATENT DOCUMENTS

| | | | | |
|---|---|---|---|---|
| WO | WO 97/25098 | | 7/1997 | |
| WO | WO 98/10828 | | 3/1998 | |
| WO | WO 98/10829 | | 3/1998 | |
| WO | WO 98/10830 | | 3/1998 | |
| WO | WO 98/10831 | | 3/1998 | |
| WO | WO 98/10832 | | 3/1998 | |
| WO | WO 99/03533 | | 1/1999 | |
| WO | WO-00/40296 | * | 7/2000 | ......... A61N/1/365 |
| WO | WO 00/42914 | | 7/2000 | ............ A61B/5/05 |
| WO | WO 00/57947 | | 10/2000 | ............ A61N/1/04 |
| WO | WO 00/57952 | | 10/2000 | ......... A61N/1/362 |

OTHER PUBLICATIONS

M.R. Franz 'Monophasic Action Potential Recordings: What are they, How can they be recorded, What is their use?', published in "Monophasic Action Potentials", Franz, Schmitt and Zrenner eds., pp. 22–39 Springer–Verlag, Berlin 1997.

H. Antoni, et al., Polarization Effects of Sinusoidal 50–Cycle Alternating Current on Membrane Potential of Mammalian Cardiac Fibres, Pflugers Arch. 314, pp. 274–291 (1970).

* cited by examiner

Primary Examiner—Carl Layno
(74) Attorney, Agent, or Firm—Cowan, Liebowitz & Latman, P.C.; William H. Dippert

(57) ABSTRACT

Apparatus for automatically controlling the delivery of excitable tissue control signals to a heart. The apparatus includes an excitable tissue control unit for delivering excitable tissue control signals to the heart, an action potential duration (APD) determining unit for receiving sensed cardiac action potential related signals. The APD determining unit determines an estimated action potential duration value from one or more action potential related signals, computes one or more excitable tissue control signal parameters, and controls the delivery of excitable tissue control signals based on the computed signal parameter(s). The cardiac action potential related signals may be cardiac close bipolar electrogram signals and cardiac monophasic action potential signals. Methods are disclosed for use with the apparatus to control the delivery of excitable tissue control signals to the heart.

133 Claims, 13 Drawing Sheets

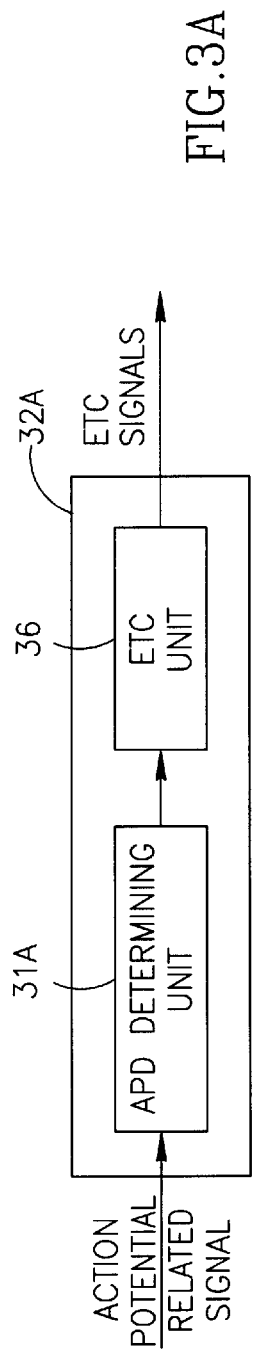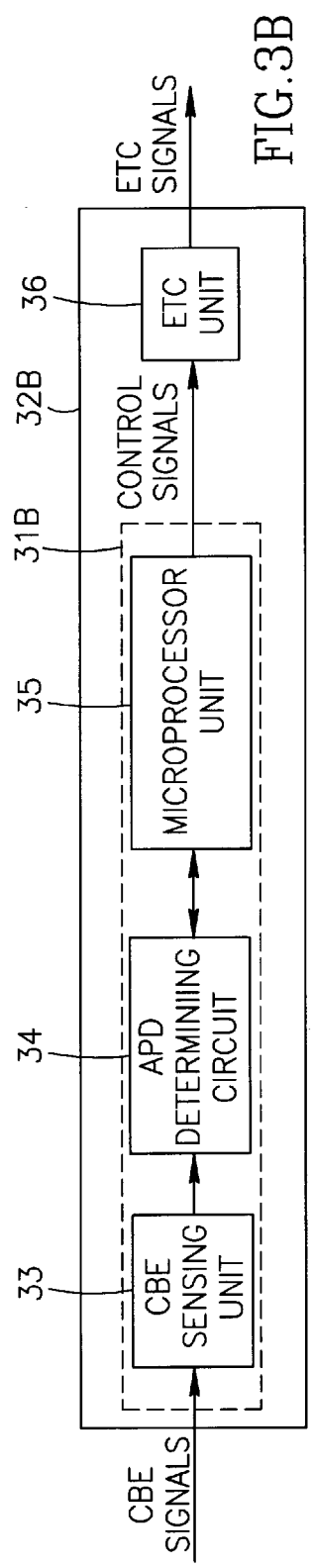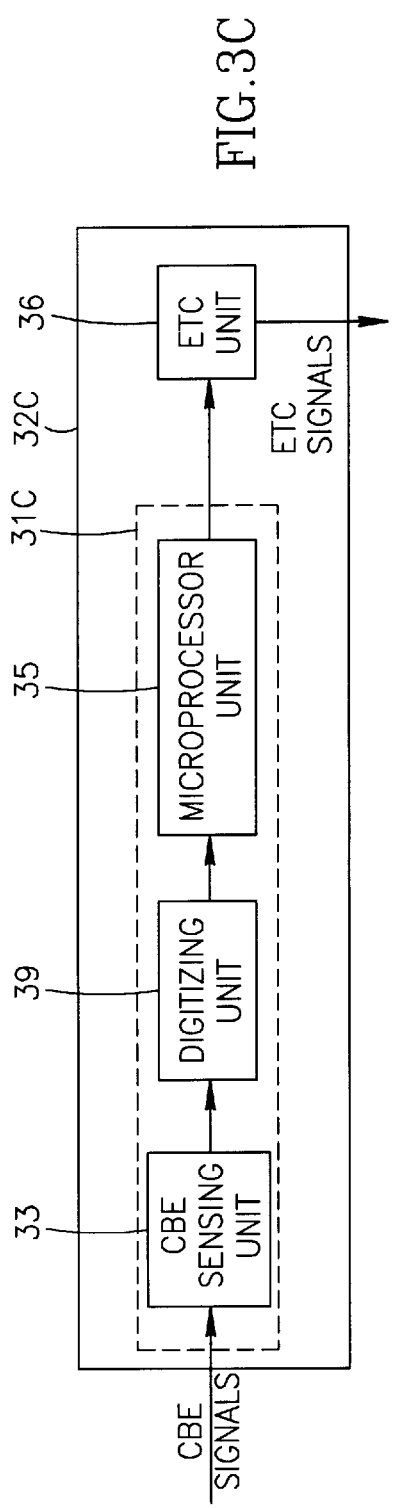

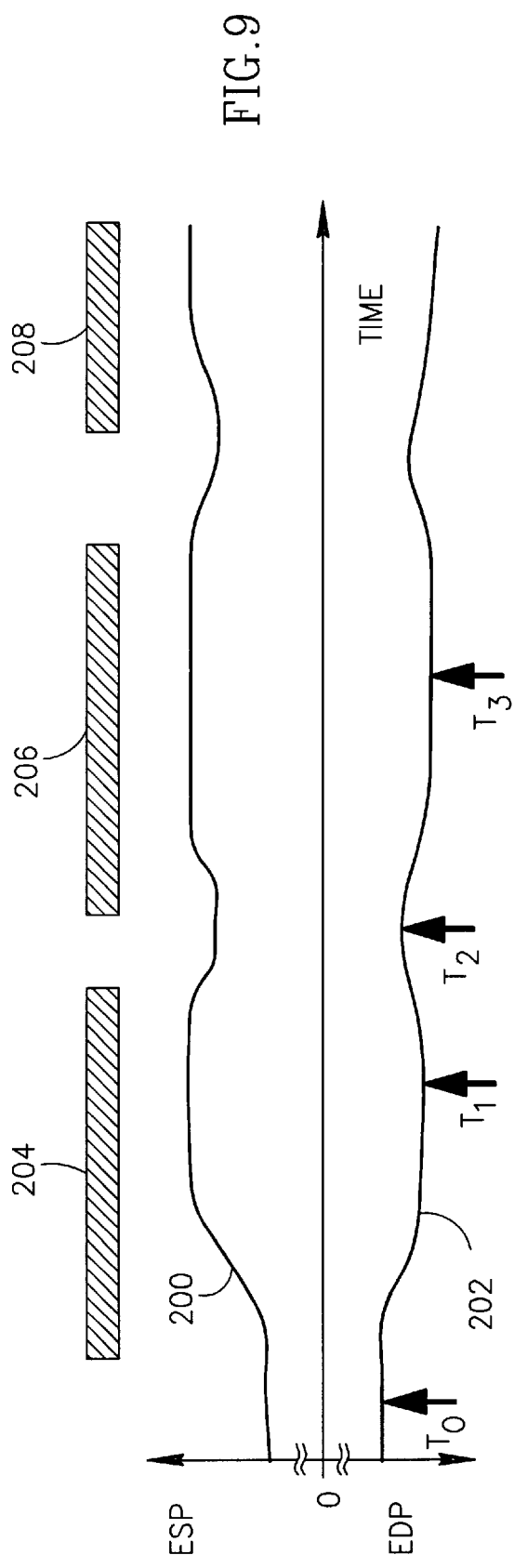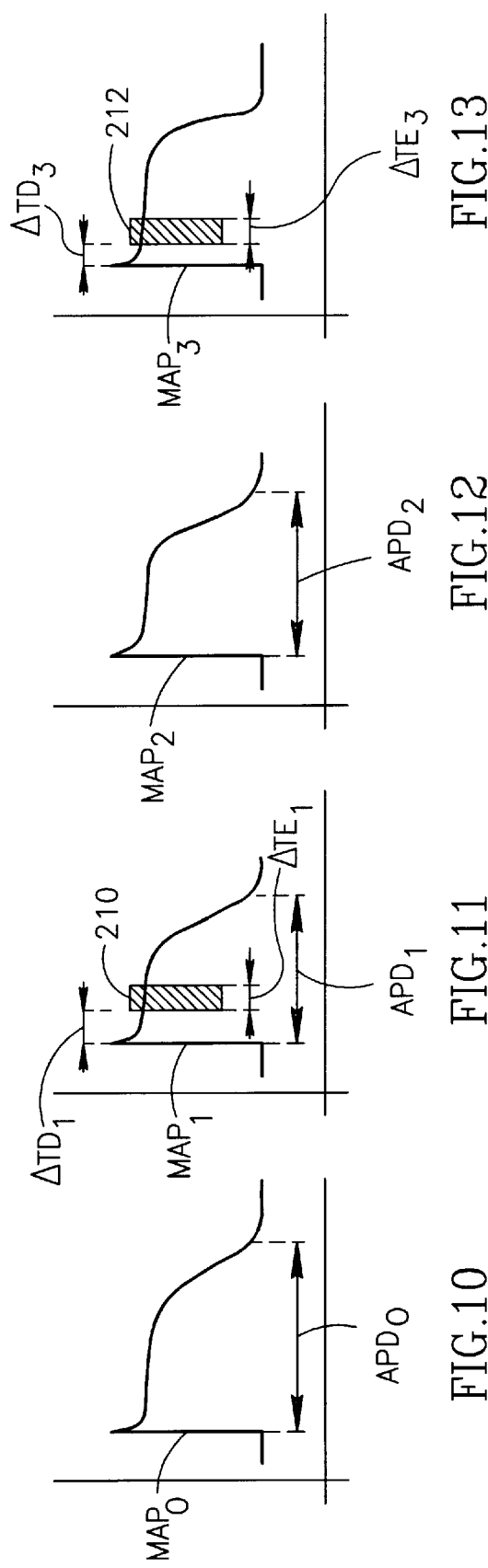

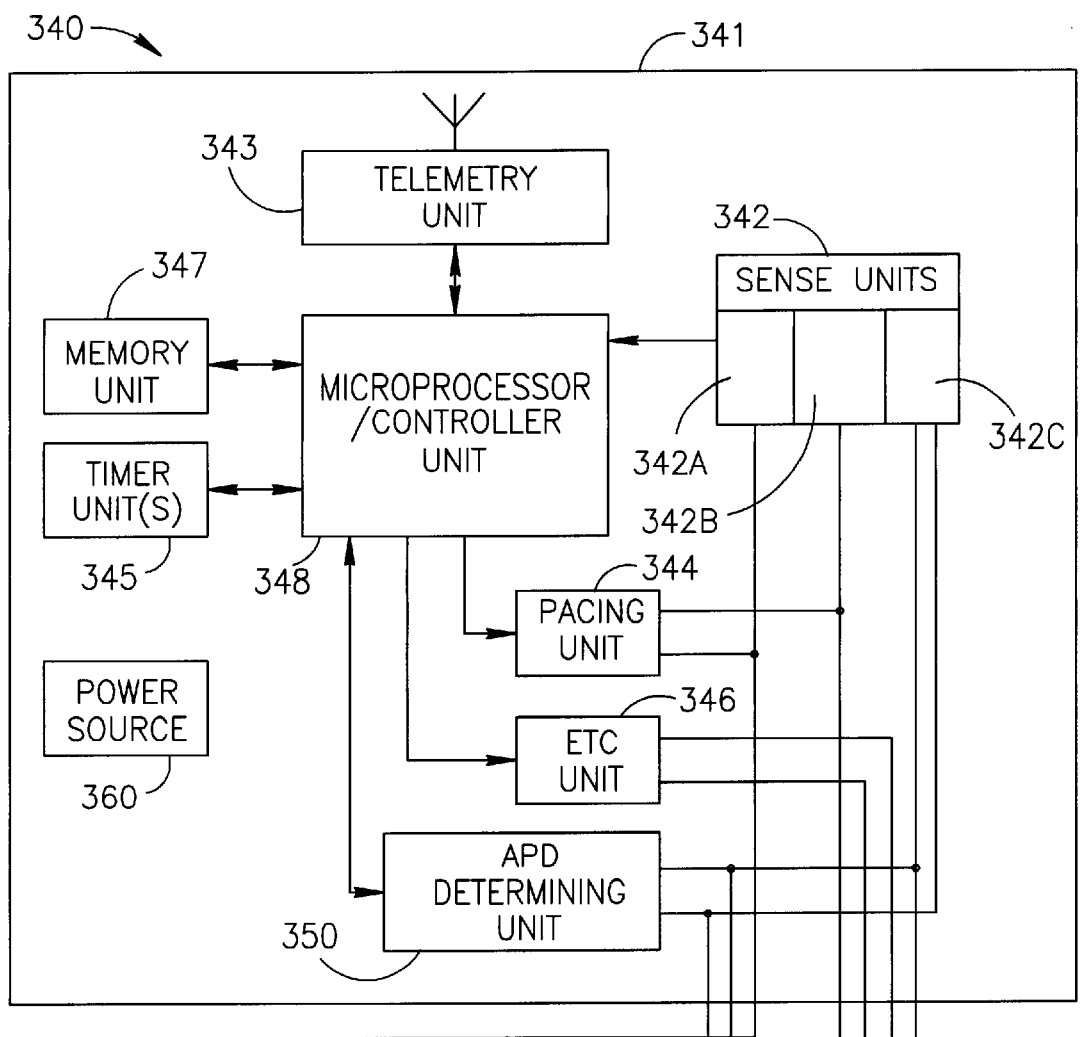
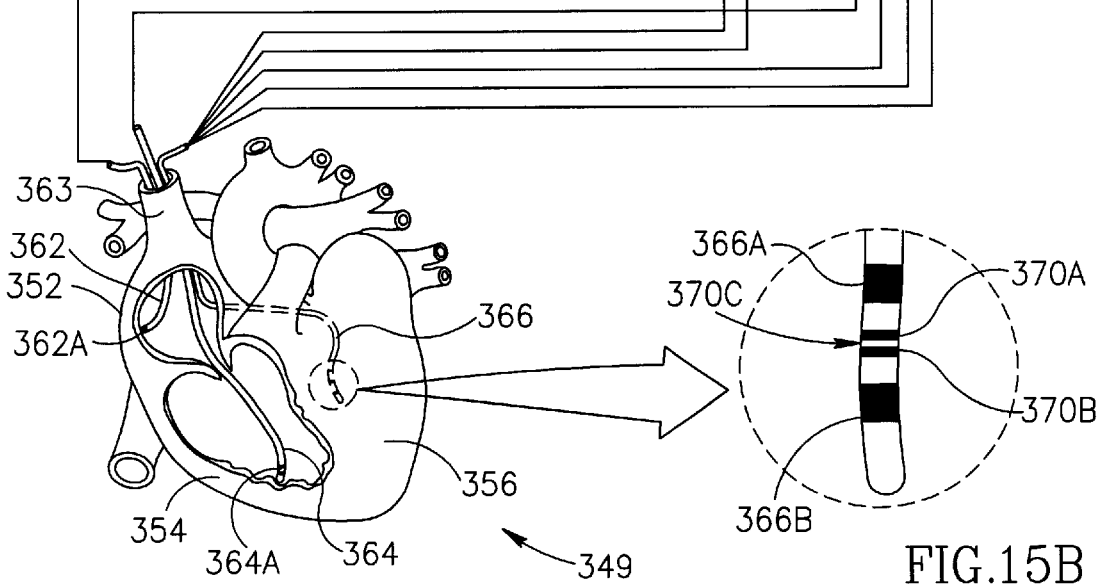
FIG.15A
FIG.15B

APPARATUS AND METHOD FOR CONTROLLING THE DELIVERY OF CONTRACTILITY MODULATING NON-EXCITATORY SIGNALS TO THE HEART

FIELD OF THE INVENTION

The present invention relates generally to the field of methods and medical devices for modulating cardiac muscle contractility and more specifically to apparatus and methods for determining the parameters of delivery of excitable tissue controller (ETC) signals under a variety of cardiac conditions.

BACKGROUND OF THE INVENTION

Excitable tissue controllers (ETCs) are devices which modulate the activity of excitable tissues by application of non-excitatory electrical stimulation to the excitable tissue through suitable electrodes in contact with the tissue. For example, ETC devices may be used, inter alia, to increase or decrease the contractility of cardiac muscle in vitro, in vivo and in situ., as disclosed in detail in PCT application, International Publication Number WO 97/25098 to Ben-Haim et al., titled "ELECTRICAL MUSCLE CONTROLLER", incorporated herein by reference. Other methods and applications of ETC devices are disclosed in PCT applications commonly-assigned to the assignee of the present application, International Publication Number WO 98/10828, titled "APPARATUS AND METHOD FOR CONTROLLING THE CONTRACTILITY OF MUSCLES" to Ben Haim et al., incorporated herein by reference, International Publication Number WO 98/10829, titled "DRUG-DEVICE COMBINATION FOR CONTROLLING THE CONTRACTILITY OF MUSCLES" to Ben Haim et al., incorporated herein by reference and International Publication Number WO 98/10830, titled "FENCING OF CARDIAC MUSCLES" to Ben Haim et al., incorporated herein by reference, International Publication Number WO 98/10831 to Ben Haim et al., titled "CARDIAC OUTPUT CONTROLLER", incorporated herein by reference.

Further applications of the ETC including devices combining cardiac pacing and cardiac contractility modulation are disclosed in PCT Application, International Publication No. WO 98/10832, titled "CARDIAC OUTPUT ENHANCED PACEMAKER" to Ben Haim et al., co-assigned to the assignee of the present application. Such ETC devices function by applying non-excitatory electrical field signals of suitable amplitude and waveform, appropriately timed with respect to the heart's intrinsic electrical activity to selected cardiac segments. The contraction of the selected segments can be modulated to increase or decrease the stroke volume of the heart. The timing of the ETC signals must be carefully controlled since application of the ETC signal to the myocardium at inappropriate times may be arrhythmogenic. The ETC signals must therefore be applied to the selected cardiac segment within a defined time interval during which the selected cardiac segment will not be stimulated by the ETC signals.

As disclosed in International Publication No. WO 98/10832, the ETC signals may be timed relative to a trigger signal which is also used as a pacing trigger, or may be timed relative to locally sensed electrogram signals.

U.S. Patent Application to Mika et al., Ser. No. 09/276, 460, Titled "APPARATUS AND METHOD FOR TIMING THE DELIVERY OF NON-EXCITATORY ETC SIGNALS TO A HEART", filed Mar. 25, 1999 and assigned to the common assignee of the present application, the entire specification of which is incorporated herein by reference, discloses a method for timing the delivery of non-excitatory ETC signals to a heart using, inter alia, an alert window period for reducing the probability of delivering an improperly timed ETC signal to the heart due to spurious detection of noise or ectopic beats.

U.S. patent application Ser. No. 09/328,068 to Mika et al., filed Jun. 8, 1999, assigned to the common assignee of the present application, titled "APPARATUS AND METHOD FOR COLLECTING DATA USEFUL FOR DETERMINING THE PARAMETERS OF AN ALERT WINDOW FOR TIMING DELIVERY OF ETC SIGNALS TO A HEART UNDER VARYING CARDIAC CONDITIONS", now U.S. Pat. No. 6,223,072, the entire specification of which is incorporated herein by reference, discloses, inter alia, apparatus and methods for collecting data from a patient's heart. The collected data is processed to obtain a data set which may be used in an ETC device for dynamically setting the parameters of an alert window used for detecting a depolarization event to trigger the delivery of ETC signals to the heart.

U.S. patent application to Mika et al., filed Jun. 23, 1999, Ser. No. 09/338,649, assigned to the common assignee of the present application, titled "APPARATUS AND METHOD FOR SETTING THE PARAMETERS OF AN ALERT WINDOW USED FOR TIMING THE DELIVERY OF ETC SIGNALS TO A HEART UNDER VARYING CARDIAC CONDITIONS", the entire specification of which is incorporated herein by reference, discloses, inter alia, apparatus and methods for using the data set obtained in U.S. patent application Ser. No. 09/328,068, now U.S. Pat. No. 6,223, 072, to Mika et al., referenced hereinabove, for dynamically setting the parameters of an alert time window on a beat by beat basis.

These methods take into account changes in the velocity of propagation of the depolarization wave in the myocardium caused by various cardiac conditions such as pacing of the heart, prior delivery of ETC signals to the myocardium and the beat to beat cycle length (which is indicative of the instantaneous heart rate).

ETC devices effect their influence on the electrochemical/ electromechanical dynamics of the tissue through electrical currents delivered to the tissue after it has been stimulated and while it is undergoing active depolarization and repolarization.

However, when attempting to control the contractility of the heart using ETC devices, currents forced through the tissue past the effective refractory period (ERP) may be arrhythmogenic.

Typically, in ETC therapy the duration of the effective refractory period and other parameters of interest such as, inter alia, the action potential duration, the dispersion of repolarization and the activation velocity are estimated under physician supervision during or after the implantation of an implanted ETC device, or after the implantation of electrodes in the patient's heart and the connection of the implanted electrodes to a non-implantable ETC device disposed outside the patient's body. Such devices are disclosed, inter alia, in U.S. patent applications Ser. Nos. 09/276,460 and 09/328,068 to Mika et al. and in U.S Patent Application to Mika et al., filed Jun. 23,1999, cited hereinabove. The ERP and the other parameters of interest may then be periodically estimated during follow-up visits of the patient Unfortunately, since the refractory period of the myocardium may change as a function of various of factors such as, inter-alia, the state of the tissue, the level of circulating hormones, such as, but not limited to cathecholamines, the presence and level of pharmacological agents, artificial cardiac stimulation (e.g. pacing), as well as the previous application of ETC signals, a-priori assessment of the duration of the ERP may not be possible.

Moreover, even if it was possible to assess a mean duration of the ERP for some of the above mentioned cardiac conditions, this only represents an average value which may not be valid for each individual cardiac beat cycle, since the ERP duration value may still fluctuate for individual beats occurring under similar cardiac conditions.

Furthermore, certain pathological conditions such as myocardial ischemia, tachycardia and premature ventricular contractions may result in gradual or even abrupt changes in the cardiac action potential parameters which may result in respective gradual or abrupt changes in the ERP duration, Such changes may increase the probability of delivery of ETC signals in the vulnerable time period outside of the ERP duration, unduly increasing the risk of induced arrhythmia.

Another problem which may be encountered during delivery of cardiac ETC therapy, is that the efficacy of the therapy may change as a result of changes in the cardiac action potential duration (APD). This stems from the fact that the ETC signal effectiveness may vary as a function of the timing of the ETC signal delivery within the non vulnerable portion of the cardiac action potential.

SUMMARY OF THE INVENTION

There is therefore provided, in accordance with a preferred embodiment of the present invention, a method for automatically controlling the delivery of excitable tissue control signals to a heart of a patient. The method includes the steps of, determining an estimated action potential duration value from at least one cardiac action potential related signal sensed at a first cardiac site of the heart, processing the estimated action potential duration value to obtain at least one excitable tissue control signal parameter, and using the at least one parameter to control the delivery of one or more excitable tissue control signals to a second cardiac site of the heart after the time of occurrence of the at least one cardiac action potential related signal of the step of determining.

Furthermore, in accordance with a preferred embodiment of the present invention, the cardiac action potential related signal is a close bipolar electrogram signal.

Furthermore, in accordance with a preferred embodiment of the present invention, the close bipolar electrogram signal includes a first signal component representing the differentiated upstroke of the fast depolarization phase of a cardiac action potential and a second signal component representing the differentiated fast repolarization phase of the cardiac action potential, and the step of determining includes determining a first time point at which the amplitude of the first signal component first crosses a first threshold value, determining a second time point at which the amplitude of the second signal component first crosses a second threshold value, and obtaining the estimated action potential duration value by determining the value of the time interval between the second time point and the first time point.

Furthermore, in accordance with a preferred embodiment of the present invention, the close bipolar electrogram signal also includes a third signal component comprising an electrical artifact induced by the delivery of an excitable tissue control signal to the second cardiac site within the duration of the at least one cardiac action potential. The method further comprises the step of processing the close bipolar electrogram signal to reduce or eliminate the third signal component.

Furthermore, in accordance with a preferred embodiment of the present invention, the third signal component is reduced or eliminated by using a method selected from signal blanking and active signal canceling.

Furthermore, in accordance with a preferred embodiment of the present invention, the close bipolar electrogram signal includes a first signal component representing the differentiated upstroke of the fast depolarization phase of a cardiac action potential and a second signal component representing the differentiated fast repolarization phase of the cardiac action potential, and the step of determining includes the steps of determining a first time point at which the amplitude of the first signal component first crosses a first threshold value going in a first direction, determining a second time point at which the amplitude of the second signal component first crosses a second threshold value going in a second direction, and obtaining the estimated action potential duration value by determining the value of the time interval between the second time point and the first time point.

Furthermore, in accordance with a preferred embodiment of the present invention, the cardiac action potential related signal is monophasic action potential signal.

Furthermore, in accordance with a preferred embodiment of the present invention, the at least one cardiac action potential related signal is a monophasic action potential signal.

Furthermore, in accordance with a preferred embodiment of the present invention, the monophasic action potential signal includes a sharp leading edge related to the fast depolarization phase of a cardiac action potential and has a maximal amplitude value, and the step of determining includes the steps of determining a first time point at which the amplitude of the sharp leading edge first crosses a first threshold value, determining the maximal amplitude value, determining a second time point at which the amplitude value of the monophasic action potential signal is equal to a fraction of the maximal amplitude value, and obtaining the estimated action potential duration value by determining the value of the time interval between the second time point and the first time point.

Furthermore, in accordance with a preferred embodiment of the present invention, the monophasic action potential signal also includes an artifact component representing an electrical artifact induced by the delivery of an excitable tissue control signal to the second cardiac site within the duration of the at least one cardiac action potential, and the method further includes the step of processing the monophasic action potential signal to reduce or eliminate the artifact component.

Furthermore, in accordance with a preferred embodiment of the present invention, the artifact component is reduced or eliminated by using a method selected from signal blanking and active signal canceling.

Furthermore, in accordance with a preferred embodiment of the present invention, the monophasic action potential signal includes a sharp leading edge related to the fast depolarization phase of a cardiac action potential and has a maximal amplitude value, and the step of determining includes the steps of high pass filtering the monophasic action potential signal to obtain a high pass filtered signal, processing the high pass filtered signal to determine a first time point at which the amplitude of the high pass filtered signal first crosses a first threshold value, low pass filtering the monophasic action potential signal to obtain a low pass filtered signal, processing the low pass filtered signal to determine the maximal amplitude value thereof, determining a second time point at which the amplitude value of the low pass filtered signal is equal to a fraction of the maximal amplitude value, and obtaining the estimated action potential duration value by determining the value of the time interval between the second time point and the first time point.

There is further provided, in accordance with a preferred embodiment of the present invention, apparatus for automatically controlling the delivery of excitable tissue control signals to a heart of a patient. The apparatus includes means for determining an estimated action potential duration value from at least one cardiac action potential related signal sensed at a first cardiac site of the heart, means for processing the estimated action potential duration value to obtain at least one excitable tissue control signal parameter, and means for using the at least one parameter to control the delivery of one or more excitable tissue control signals to a second cardiac site of the heart after the time of occurrence of the at least one cardiac action potential related signal of the step of determining.

There is further provided, in accordance with a preferred embodiment of the present invention, Apparatus for automatically controlling the delivery of excitable tissue control signals to a heart of a patient. The apparatus includes an excitable tissue control unit for delivering the excitable tissue control signals to a first site of the heart, an action potential duration determining unit operatively connected to the excitable tissue control unit for receiving action potential related signals sensed at a second site of the heart, determining an estimated action potential duration value from at least one of the action potential related signals, computing at least one excitable tissue control signal parameter and controlling the delivery at least one of the excitable tissue control signals based on the at least one excitable tissue control signal parameter. The apparatus further includes a power source for energizing the excitable tissue control unit and the action potential duration determining unit.

Furthermore, in accordance with a preferred embodiment of the present invention, the action potential duration determining unit includes, a close bipolar electrogram sensing unit for sensing close bipolar electrogram signals at the second site of the heart, a digitizing unit operatively connected to the close bipolar electrogram sensing unit for digitizing the close bipolar electrogram signals sensed by the close bipolar electrogram sensing unit to provide digitized close bipolar electrogram signals, and a microprocessor unit operatively connected to the digitizing unit and the excitable tissue control unit, for receiving the digitized close bipolar electrogram signals, determining an estimated action potential duration value from at least one of the digitized close bipolar electrogram signals, computing at least one excitable tissue control signal parameter from the estimated action potential duration value and controlling the delivery of at least one of the excitable tissue control signals based on the at least one excitable tissue control signal parameter.

Furthermore, in accordance with a preferred embodiment of the present invention, the at least one of the action potential related signals includes at least one cardiac close bipolar electrogram signal, and the action potential duration determining unit includes, a close bipolar electrogram sensing unit for sensing close bipolar electrogram signals at the second site of the heart, an action potential duration determining circuit operatively connected to the close bipolar electrogram sensing unit for receiving the close bipolar electrogram signals, processing the close bipolar electrogram signals to provide estimated action potential duration values corresponding to the close bipolar electrogram signals, and a microprocessor unit operatively connected to the action potential duration determining circuit and to the excitable tissue control unit, for receiving the estimated action potential duration values, computing at least one excitable tissue control signal parameter from at least one of the estimated action potential duration values and controlling the delivery of at least one of the excitable tissue control signals based on the at least one excitable tissue control signal parameter.

Furthermore, in accordance with a preferred embodiment of the present invention, the closed bipolar electrogram sensing unit includes a differential amplifier connectable to a pair of electrodes for sensing the close bipolar electrogram signals.

Furthermore, in accordance with a preferred embodiment of the present invention, the action potential duration determining circuit includes a first band pass filter operatively connected to the output terminal of the differential amplifier and adapted to preferentially pass a first frequency range corresponding to a first high frequency component of the close bipolar electrogram signals and to produce a first filtered signal, a second band pass filter operatively connected to the output terminal of the differential amplifier and adapted to preferentially pass a second frequency range corresponding to a second low frequency component of the close bipolar electrogram signals and to produce a second filtered signal, a first tunable threshold circuit operatively connected to the output terminal of the first band pass filter for generating a first trigger signal when the filtered signal crosses a first threshold value, a second tunable threshold circuit operatively connected to the output terminal of the second band pass filter for generating a second trigger signal when the second filtered signal crosses a second threshold value, and an edge activated binary counter operatively connected to the first tunable threshold circuit and to the second tunable threshold circuit for receiving and processing the first trigger signal and the second trigger signal to provide an output signal representing an estimated action potential duration value.

Furthermore, in accordance with a preferred embodiment of the present invention, the action potential duration determining unit includes, a monophasic action potential sensing unit for sensing monophasic action potential signals at the second site of the heart, a digitizing unit operatively connected to the monophasic action potential sensing unit for digitizing the monophasic action potential signals sensed by the monophasic action potential sensing unit to provide digitized monophasic action potential signals, and a microprocessor unit operatively connected to the digitizing unit and the excitable tissue control unit for receiving the digitized monophasic action potential signals, determining an estimated action potential duration value from at least one of the digitized monophasic action potential signals, computing at least one excitable tissue control signal parameter from the estimated action potential duration value and controlling the delivery of at least one of the excitable tissue control signals based on the at least one excitable tissue control signal parameter.

Furthermore, in accordance with a preferred embodiment of the present invention, the microprocessor is adapted to receive the digitized monophasic action potential signal and to obtain therefrom a time value usable as the approximate starting time point of the cardiac action potential corresponding with the currently sensed monophasic action potential signal.

Furthermore, in accordance with a preferred embodiment of the present invention, the digitized monophasic action potential signal also includes an artifact component representing an electrical artifact induced by the delivery of an excitable tissue control signal to the second cardiac site within the duration of sensing the monophasic action potential signal, and the microprocessor unit is adapted for processing the digitized monophasic action potential signal to reduce or eliminate the artifact component.

Furthermore, in accordance with a preferred embodiment of the present invention, the at least one excitable tissue control signal parameter computed by the microprocessor unit is selected from the delay between the detection of a cardiac action potential and the initiation of an excitable tissue control signal, the duration of the excitable tissue control signal, the intensity of the excitable tissue control signal, the waveform of the excitable tissue control signal, the polarity of the excitable tissue control signal and any combination thereof.

Furthermore, in accordance with a preferred embodiment of the present invention, the at least one excitable tissue control signal parameter is the delay between the detection of a cardiac action potential and the initiation of the excitable tissue control signal, and the microprocessor unit is adapted for computing the delay by multiplying the estimated action potential duration value by a first coefficient $\alpha$ to obtain a first computed value, and by adding a first constant $C_1$ to the first computed value.

Furthermore, in accordance with a preferred embodiment of the present invention, the first coefficient $\alpha$ is empirically determined for the patient.

Furthermore, in accordance with a preferred embodiment of the present invention, the at least one excitable tissue control signal parameter is the duration of an excitable tissue control signal, and wherein the duration is computed by multiplying the estimated action potential duration value by a second coefficient $\beta$ to obtain a second computed value, and by adding a second constant $C_2$ to the second computed value.

Furthermore, in accordance with a preferred embodiment of the present invention, the second coefficient $\beta$ is empirically determined for the patient.

Furthermore, in accordance with a preferred embodiment of the present invention, the monophasic action potential signal includes a sharp leading edge related to the fast depolarization phase of a cardiac action potential and has a maximal amplitude value. The microprocessor unit is adapted to determine a first time point at which the amplitude of the sharp leading edge first crosses a first threshold value, determine the maximal amplitude value, determine a second time point at which the amplitude value of the monophasic action potential signal is equal to a fraction of the maximal amplitude value, and obtain the estimated action potential duration value by determining the value of the time interval between the second time point and the first time point.

Furthermore, in accordance with a preferred embodiment of the present invention, the second time point is the time point at which the amplitude value of the monophasic action potential signal is equal to 10% of the maximal amplitude value and the estimated action potential duration value is the $MAP_{90}$ value.

Furthermore, in accordance with a preferred embodiment of the present invention, the at least one of the action potential related signals includes at least one cardiac monophasic action potential, and the action potential duration determining unit includes, a monophasic action potential sensing unit for sensing monophasic action potential signals at the second site of the heart, an action potential duration determining circuit operatively connected to the monophasic action potential sensing unit for receiving the monophasic action potential signals and processing the monophasic action potential signals to provide estimated action potential duration values corresponding to the monophasic action potential signals, and a microprocessor unit operatively connected to the action potential duration determining circuit and to the excitable tissue control unit for receiving the estimated action potential duration values, computing at least one excitable tissue control signal parameter from at least one of the estimated action potential duration values and controlling the delivery of at least one of the excitable tissue control signals based on the at least one excitable tissue control signal parameter.

Furthermore, in accordance with a preferred embodiment of the present invention, the microprocessor is adapted to compute the average estimated action potential duration by using a moving average program selected from a weighted moving average program and a non-weighted moving average program.

Furthermore, in accordance with a preferred embodiment of the present invention, the moving average program is implemented using an implementation method selected from a finite impulse response implementation method and an infinite impulse response implementation method.

Furthermore, in accordance with a preferred embodiment of the present invention, the microprocessor unit is adapted to disable the delivery of at least one of the excitable tissue control signals to the second site of the heart if the estimated action potential duration value is smaller than a minimal acceptable action potential duration value.

Furthermore, in accordance with a preferred embodiment of the present invention, the first cardiac site is in the vicinity of the second cardiac site.

Finally, in accordance with a preferred embodiment of the present invention, the first cardiac site and the second cardiac site are located in or about the left ventricle of the heart.

BRIEF DESCRIPTION OF THE DRAWINGS

The invention is herein described, by way of example only, with reference to the accompanying drawings, in which like components are designated by like reference numerals, wherein:

FIGS. 3A–3E are schematic functional block diagrams useful in understanding different devices for controlling the parameters of ETC signals based on estimating the cardiac action potential duration, in accordance with a preferred embodiment of the present invention;

FIGS. 9–13 are schematic graphs useful in understanding a method for controlling the ETC signal parameters by determining the estimated action potential duration during a time period in which ETC signal delivery is interrupted, in accordance with another preferred embodiment of the present invention;

FIG. 15A is a schematic diagram illustrating a device for controlling the delivery of excitable tissue control signals to the heart of a patient based on close bipolar electrogram sensing, and for pacing the heart, in accordance with a preferred embodiment of the present invention.

FIG. 15B is a schematic diagram illustrating an enlarged view of the lead and electrodes used for closed bipolar sensing and for delivering ETC signals, in conjunction with the device illustrated in FIG. 15A.

DETAILED DESCRIPTION OF THE INVENTION

Notation Used Throughout

Figure 1A:
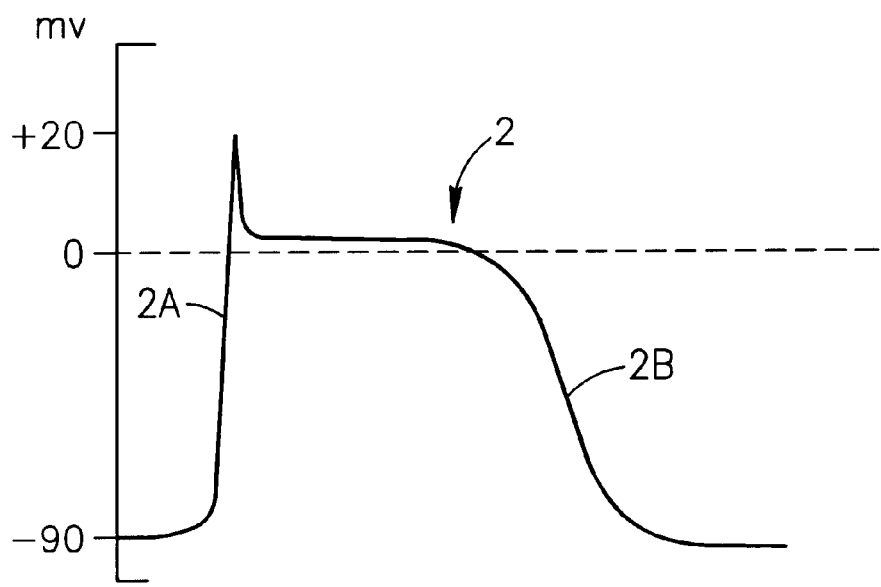
FIGS. 1A–1C are schematic graphs illustrating the relationship between an intracellularly recorded action potential signal, a monophasic action potential signal and a close-bipolar electrogram signal recorded in a heart.

The following notation is used throughout this document.

| Term | Definition |
| --- | --- |
| LV | Left Ventricle |
| RV | Right Ventricle |
| RA | Right Atrium |
| APD | Action Potential Duration |
| SVC | Superior Vena Cava |
| CS | Coronary Sinus |
| GCV | Great Cardiac Vein |
| ESP | End Systolic Pressure |
| EDP | End Diastolic Pressure |
| MAP | Monophasic Action Potential |
| CBE | Close Bipolar Electrogram |
| ETC | Excitable Tissue Control |
| CCM | Cardiac Contractility Modulating |
| ERP | Effective Refractory Period |

It is noted that throughout this application the terms "ETC signal" and "CCM signal" are interchangeably and synonymously used to define an electrical current or voltage signal applied to cardiac tissue within the effective refractory period of a cardiac action potential occurring in the cardiac tissue to modulate the cardiac contractility of the cardiac tissue without evoking a propagating cardiac action potential in the cardiac tissue. Similarly, the terms "ETC device" and "CCM device" are interchangeably and synonymously used to define a device for applying such ETC signals or CCM signals to the heart to modulate or control cardiac contractility. Similarly the plural terms "ETC signals" and "ETC devices" are synonymous to and interchangeable with the corresponding plural terms "CCM signals" and "CCM devices".

The inventors have noticed that certain methods capable of direct assessment of the timing of the depolarization and repolarization phases of the cardiac action potential in cardiac tissue may be applied for controlling the application of ETC signals to the heart in near real-time. Such methods may be advantageously applied to modify the parameters controlling the delivery of ETC signals to the heart based on the real time or near real time assessment of the timing of the depolarization and repolarization phases of the cardiac tissue.

Methods for Estimating Cardiac Action Potential Duration

In accordance with one preferred embodiment of the present invention, acute or chronic recording of the cardiac monophasic action potential (MAP) is used for estimating the action potential duration (APD). The estimated APD is used for controlling the parameters of the ETC signals delivered to the heart in near real-time as is disclosed in detail hereinafter. The method may apply acute or chronic MAP recording depending on whether the ETC device is a device for providing short term cardiac ETC therapy or is a chronically implanted ETC device for providing long term cardiac ETC therapy.

U.S. patent application, Ser. No. 09/237,568 to D. Prutchi, now U.S. Pat. No. 6,152,882, filed Jan. 26,1999, titled "APPARATUS AND METHODS FOR CHRONIC MEASUREMENT OF MONOPHASIC ACTION POTENTIALS", assigned to the assignee of the present application, incorporated herein by reference in its entirety, discloses, inter alia, methods and devices for chronic cardiac MAP recording. This Application includes detailed theoretical background, references, and experimental evidence on the use of various methods for determining MAP.

In accordance with another preferred embodiment of the present invention, a close bipolar recording electrode is used for obtaining a close-bipolar electrogram signal which may be used for estimating the APD. The estimated APD is used for controlling the parameters of the ETC signals delivered to the heart in near real-time, as is disclosed in detail hereinafter.

Figure 1B:
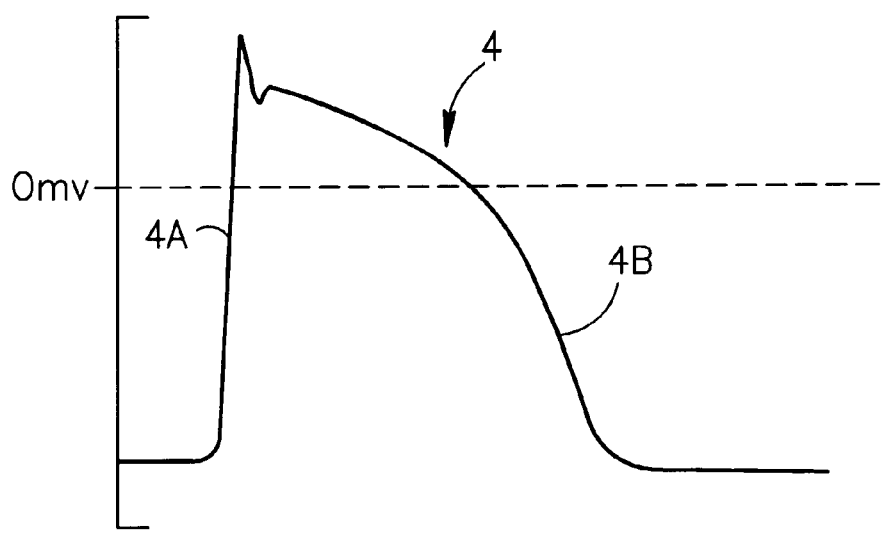
Figure 1C:
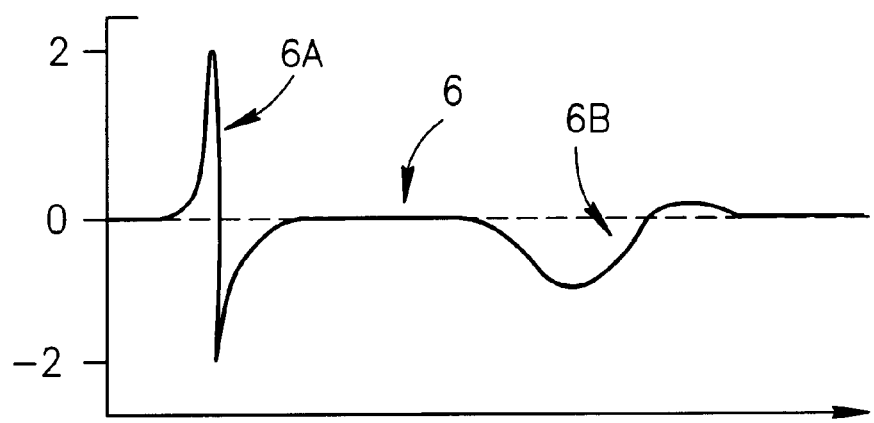

Reference is now made To FIGS. 1A–1C which are schematic graphs illustrating the relationship between an intracellularly recorded action potential signal, a monophasic action potential signal and a close-bipolar electrogram signal recorded in a heart. The horizontal axis common to FIGS. 1A–1C represents time (in arbitrary units).

In FIG. 1A, the vertical axis represents the signal amplitude in millivolts and the curve 2 schematically represents the time course of the intracellularly recorded cardiac action potential. As is well known in the art, the part 2A of curve 2 represents the fast depolarization phase of the cardiac action potential and the part 2B of the curve 2 represents the fast repolarization phase of the cardiac action potential.

In FIG. 1B, the vertical axis represents the signal amplitude in millivolts and the curve 4 schematically represents the time course of a recorded cardiac monophasic action potential. The part 4A of the MAP signal curve 4, is approximately correlated with (though not necessarily identical to) the depolarization phase of the intracellular action potential represented by part 2A of curve 2, and the part 4B of the MAP signal curve 4, is approximately correlated with (though not necessarily identical to) the fast repolarization phase of the intracellular action potential represented by the part 2B of curve 2.

In FIG. 1C, the vertical axis represents the signal amplitude in millivolts, and the curve 6 schematically represents the time course of a cardiac close-bipolar electrogram (CBE) signal.

The curve 6 of FIG. 1C results from spatial and temporal differentiation of the currents generated in the cardiac tissue by a propagating action potential. The curve 6 contains information indicative of the timing of the fast depolarization phase and the fast repolarization phase of the cardiac action potential in the region near the recording site of the close bipolar electrode sensor (not shown). The part 6A of the CBE signal 6 correlates with the depolarization phase of the intracellular action potential represented by part 2A of curve 2, and the part 6B of the CBE signal 6, is correlated with the fast repolarization phase of the intracellular action potential represented by the part 2B of curve 2.

Methods and devices suitable for performing close-bipolar electrogram recording in the heart are disclosed in detail in co-pending U.S patent application Ser. No. 09/280, 486, to Yuval Mika et al., filed Mar. 30, 1999, titled "BIPOLAR SENSOR FOR MUSCLE TISSUE ACTION POTENTIAL DURATION ESTIMATION", incorporated herein by reference in its entirety.

As schematically represented in FIGS. 1A and 1B, the MAP signal curve 4 reflects the duration, as well as the approximate shape and timing of the depolarization and repolarization phases of the intracellularly recorded action potential curve 2. Thus, the information included in the features of the MAP signal is indicative of the refractory period of the myocardium at or near the site of recording and may be used to dynamically control the initiation and the termination of the ETC signal delivery.

Furthermore, while it is apparent from FIG. 1C that, while the close-bipolar electrogram signal represented by curve 6 of FIG. 1C does not reflect the full dynamics and features of the intracellularly recorded action potential represented by the curve 2 of FIG. 1A, it may be used for approximating the APD to provide an assessment of the ERP duration as is disclosed in detail hereinafter.

Thus, the method of the present invention includes the step of determining of a parameter representative of the APD by using data obtained from MAP signal recording or from CBE signal recording.

Methods for estimating APD from MAP recordings are well known in the art. For example a method for estimating APD from MAP recordings has been described in an article by M. R. Franz, titled "Monophasic Action Potential Recordings: What Are They, How Can They Be Recorded, What Is Their Use?", published in "Monophasic Action Potentials", Franz, Schmitt and Zrenner eds., pp. 22–39 Springer-Verlag, Berlin 1997.

Figure 2A:
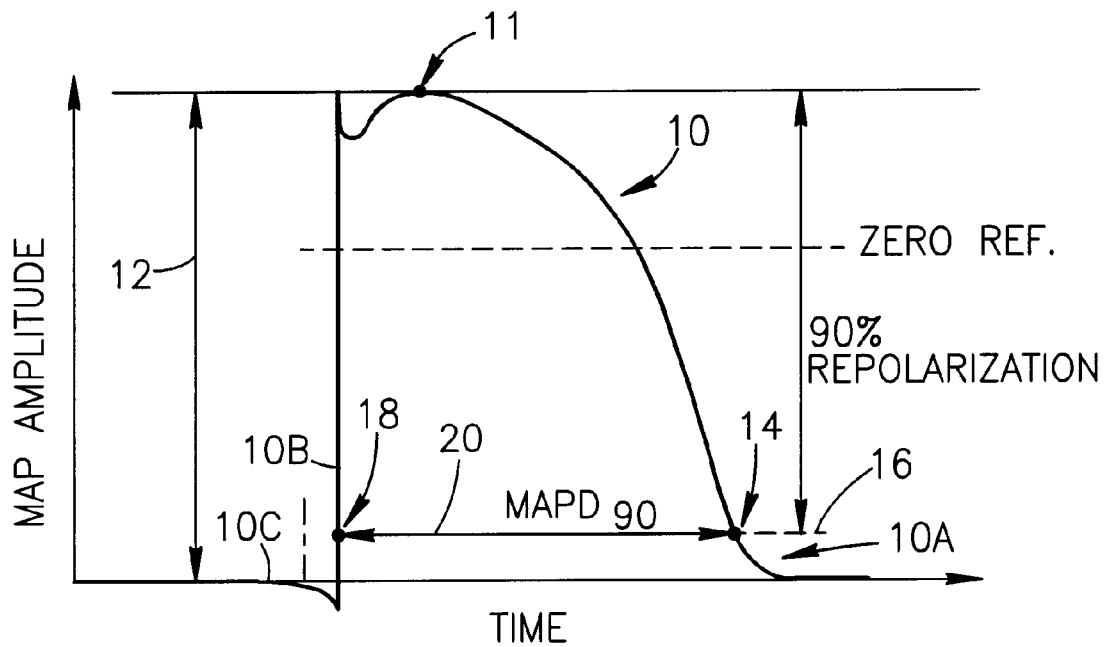
FIG. 2A is a schematic diagram illustrating a prior art method for determining from a measured cardiac monophasic action potential the value of a parameter proportional to the cardiac action potential duration.

Reference is now made to FIG. 2A which is a schematic graph illustrating a prior art method for determining from a measured cardiac monophasic action potential the value of a parameter proportional to the cardiac action potential duration. The method is based on the article by Franz referenced hereinabove. The vertical axis represents the MAP amplitude in arbitrary units and the horizontal axis represents time in arbitrary units. The curve 10 represents the MAP signal. The part 10C represents the MAP signal baseline. The point 11 represents the MAP maximal amplitude as measured from the baseline 10C. Since the asymptotic nature of the part 10A representing the repolarization phase of the MAP signal makes precise measurement of the APD difficult, the APD is often estimated by finding the MAP amplitude 12 as illustrated in FIG. 2A, finding the point 14 at which the line 16 representing a MAP repolarization level of 90% of the MAP amplitude 12 intersects the part 10A of the curve 10, finding the point 18 at which the line 16 intersects the part 10B of the curve 10, wherein the part 10B is the sharp leading edge representing the fast depolarization phase of the MAP signal curve 10, and computing the interval 20 representing the difference between the time values associated with the points 14 and 18.

The interval 20 between the time points 16 and 18 is defined as $MAPD_{90}$ which is a parameter proportional to the MAP duration. The duration of the $MAPD_{90}$ is proportional to the APD of the cardiac action potential at the site of MAP measurement and may thus be used in the method for controlling the delivery of ETC signals as is disclosed in detail hereinbelow.

It will be appreciated by those skilled in the art, that, while the value of $MAPD_{90}$ determined as disclosed by Franz is suitable for use with the method of the present invention, various modifications of the Franz method may be used if desired, to obtain other parameters such as $MAPD_{80}$ or $MAPD_{70}$ (or other different suitable parameters) by using a line representing the 80% or 70% repolarization level, respectively, of the MAP amplitude 12, instead of the line 16 of FIG. 2A. Such variations of the determined parameter may be desirable in cases of variations in the shape of the MAP signal which is recorded from the heart of the patient.

It is noted that, while the method of Franz or variations thereof may be used to obtain a parameter representative of the APD, other methods known in the art for computing a parameter correlated with the APD from the MAP signal may also be used. Thus, in accordance with the present invention, many other methods for calculating a parameter correlated with the APD from the MAP signal may be used as long as the calculated parameter is correlated to the cardiac APD.

Figure 2B:
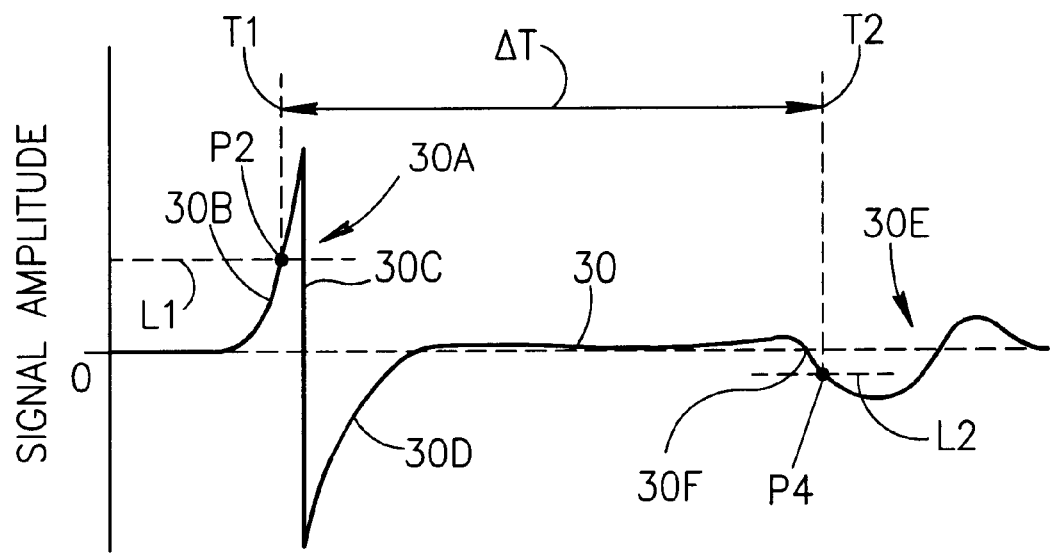
FIG. 2B is a schematic graph useful in understanding a method for determining from a cardiac close-bipolar electrogram signal the value of a parameter proportional to the cardiac action potential duration.

Reference is now made to FIG. 2B which is a schematic graph useful in understanding a method for determining from a cardiac close-bipolar electrogram signal the value of a parameter proportional to the cardiac action potential duration. The vertical axis represents the CBE signal amplitude in arbitrary units and the horizontal axis represents time in arbitrary units. The curve 30 represents the CBE signal. The CBE signal includes a first component 30A which is typically biphasic but may also be multiphasic (not shown). The first component 30A represents the differentiation of the fast depolarizing phase of the cardiac action potential at the site of recording. Typically, the component 30A starts with an positive going deflection 30B, peaks at a maximum amplitude, continues as a negative going part 30C, crosses the zero level in a negative going direction peaks again and returns towards the zero level in part 30D.

The curve 30 also includes a second later component 30E which is typically biphasic but may also be multiphasic (not shown). The second component 30E represents the differentiation of the fast repolarizing phase of the cardiac action potential at the site of recording. Typically, the second component 30E starts with a negative going part 30F which peaks at a minimum amplitude and then returns towards the baseline level.

To determine a parameter value proportional to the APD, the method finds the value of the time point T1 at which the amplitude of the positive going signal part 30B of the first signal component 30A crosses a first threshold level represented by the horizontal dashed line L1. The point P2 represents the point at which the signal part 30B crosses the first threshold level L1. The method then finds the value of the time point T2 at which the amplitude of the negative going signal part 30F of the second signal component 30E crosses a second threshold level represented by the horizontal dashed line L2. The point P4 represents the point at which the signal part 30F crosses the second threshold level L2.

The method then computes the time interval $\Delta T$ as $\Delta T = T2 - T1$. The computed parameter $\Delta T$ is proportional to the APD and may therefor be used as an estimate of the APD.

It is noted that, while the time points T1 and T2 are determined by detecting the time of crossing of the corresponding threshold levels L1 and L2, respectively, other different or additional detection criteria may also be used. For example, the slope of the signal part 30B computed at the point P2 may have to be positive or may have to be within a specified range of positive values. Similarly, the slope of the signal part 30F computed at the point P4 may have to be negative or may have to be within a specified range of negative values.

Additionally, multiple detection criteria related to the shape of the signal components 30A and 30E may be used. For example, the value of T1 may be accepted for calculating $\Delta T$ only if the signal part 30D crosses a third threshold level (not shown) and the slope at the threshold crossing point is positive or is within a specified range of positive values. Such a method may decrease the probability of false detection of a spurious signal or noise.

It will be appreciated by those skilled in the art that, many different signal detection methods may be used to compute $\Delta T$. For example, T1 may be computed as the time point at which the amplitude of the signal part 30B is 50% of the peak positive value of the first signal component 30A, and T2 may be computed as the time point at which the amplitude of the signal part 30B is 50% of the peak negative value of the second signal component 30E. Such a method may have an advantage in cases in which the CBE signal baseline level shifts with time, because it determines T1 and T2 from the values of the difference between signal baseline and signal peak components, which differences are less sensitive to baseline shift than simple threshold crossing measurements.

It is noted that the shape and polarity of the CBE signal depends on the polarity of the electrodes which is arbitrarily selected and on the direction of propagation of the myocardial depolarization wave at the CBE signal recording site. Therefore, If the polarity of the electrodes used in recording the CBE signal is reversed, the polarity of the recorded CBE signal is also reversed such that negative going and positive going signals or signal parts are reversed. In such a case the computation disclosed hereinabove is suitably adapted to the reversal. Thus, the maximum or minimum points of the positive or negative peaks of both first CBE signal component 30A and second CBE signal component 30B are generally referred to as extremum points hereinafter and may be positive or negative values depending on the CBE electrode polarity.

It is further noted that, the method of computing $\Delta T$ is not limited to using half extremum (such as 50% maximum or 50% minimum) values as disclosed above, but may be suitably adapted to use other specified fractions of the peak extremum values such as, but not limited to, 40% maximum, 60% minimum, or any other suitable extremum fraction values. The precise method and amplitude values of the points P2 and P4 used in computing $\Delta T$ may depend, inter alia, on the shape and amplitude values of the recorded CBE signal, on the noise level and on the degree of expected baseline shift of the CBE signal.

It is noted that, the computational methods for computing the APD correlated parameter such as the $\Delta T$ parameter disclosed are not limited to the methods disclosed hereinabove and that any method known in the art using any combination of threshold crossing levels and/or slope values or slope range values is acceptable for use in the present invention as long as it computes a suitable parameter which is correlated to the cardiac action potential duration at or near the site of the CBE sensing electrode.

Since the repolarization component 30E is typically a low amplitude component of the close-bipolar electrogram signal, it is preferably detected using a dedicated signal processing chain.

Examples of Circuits for Determining Estimated APD

Reference is now made to FIGS. 3A–3E which are schematic functional block diagrams useful in understanding the different devices for controlling the parameters of ETC signals based on estimating the cardiac action potential duration, in accordance with a preferred embodiment of the present invention.

FIG. 3A is a schematic functional block diagram useful in understanding the general configuration of a device 32A for controlling the parameters of ETC signals based on estimating the cardiac action potential duration, in accordance with a preferred embodiment of the present invention. The device 32A includes an APD determining unit 31A which receives as input a signal related to the cardiac action potential sensed in the heart of a patient (patient not shown) and determines from the action potential related signal a parameter which is related to the cardiac action potential duration and is therefore representative of the cardiac action potential duration. The device 32A also includes an ETC unit 36 suitably connected to the APD determining unit 31A. The ETC unit 36 is capable of delivering ETC signals to the heart for controlling cardiac contractility. The ETC unit 36 is controlled by control signals generated by the APD determining unit 31A. The cardiac action potential related signal may be a cardiac MAP signal or a cardiac CBE signal as disclosed in detail hereinafter.

Figure 3D:
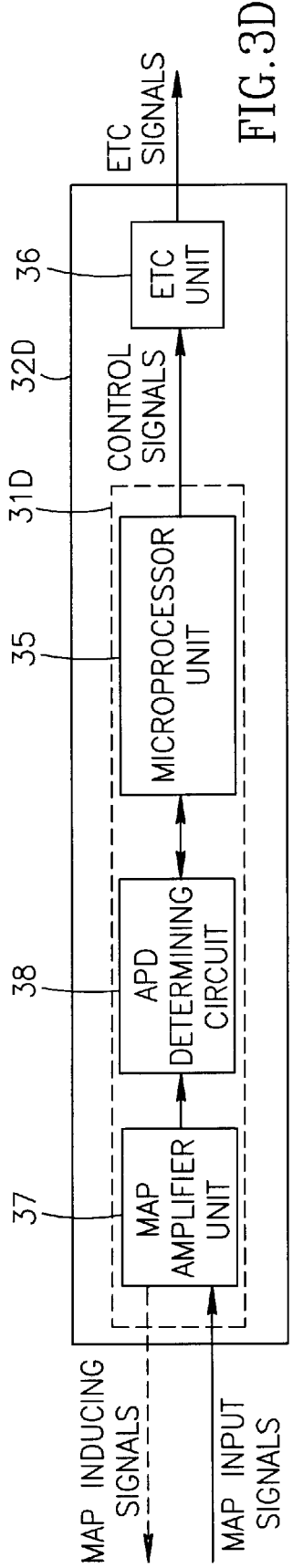
Figure 3E:
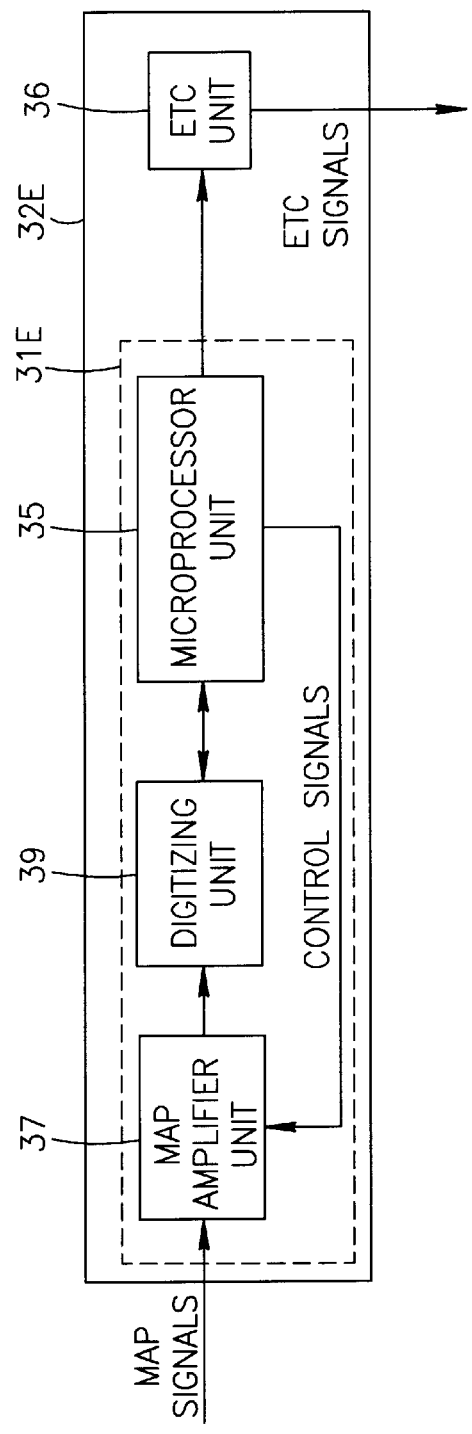

FIGS. 3B and 3C are diagrams of two different alternative implementations of the a device 32A of FIG. 3A in which the cardiac action potential related signal is a cardiac CBE signal. FIGS. 3D and 3E are diagrams of two additional alternative implementations of the a device 32A of FIG. 3A in which the cardiac action potential related signal is a cardiac MAP signal.

In the preferred embodiment illustrated in FIG. 3B, the device 32B includes an APD determining unit 31B and an ETC unit 36 capable of delivering ETC signals to the heart for controlling cardiac contractility. the APD determining unit 31B includes a CBE sensing unit 33 which operates to sense and amplify a CBE signal in or about the heart. The amplified CBE signal is sent as output to an APD determining circuit 34 which determines from the CBE signal a parameter proportional to the cardiac APD (an estimated APD) in the vicinity of the location at which the CBE is sensed. The value of the parameter proportional to the APD is output to a controller or microprocessor 35 for processing. The microprocessor 35 is connected to the ETC unit 36. The ETC unit 36 is controlled by control signals generated by the microprocessor 35. The microprocessor 35 uses the value of the APD related parameter to compute the parameters of the ETC signal delivered to the heart. The computed ETC parameters may include the ETC signal starting time, the ETC signal duration, ETC signal amplitude and the ETC signal waveform as is disclosed in detail hereinafter.

In the preferred embodiment illustrated in FIG. 3C, the device 32C includes an APD determining unit 31C and an ETC unit 36 capable of delivering ETC signals to the heart for controlling cardiac contractility. The APD determining unit 31C includes a CBE sensing unit 33, a digitizing unit 39 connected thereto and a microprocessor unit 35 connected to the digitizing unit 39 and to the ETC unit 36. The CBE sensing unit 33 operates to sense and amplify a CBE signal in or about the heart. The amplified CBE signal is sent as output to the digitizing unit 39 for digitizing. The digitized CBE signal is sent to the microprocessor unit 35 which processes the digitized signal and determines a parameter proportional to the cardiac APD (an estimated APD) in the vicinity of the location at which the CBE is sensed. The microprocessor 35 uses the value of the APD related parameter to compute the parameters of the ETC signal delivered to the heart. The computed ETC signal parameters may include the ETC signal starting time, the ETC signal duration, the ETC signal amplitude and the ETC signal waveform as is disclosed in detail hereinafter.

In the preferred embodiment illustrated in FIG. 3D, the device 32D includes an APD determining unit 31D and an ETC unit 36 capable of delivering ETC signals to the heart for controlling cardiac contractility. The device 32D is similar in operation to the device 32B, except that instead of the CBE sensing unit 33 it includes a MAP amplifier unit 37 for measuring a cardiac MAP signal and instead of the APD determining circuit 34 it includes an APD determining circuit 38 which is adapted for determining a parameter proportional to the APD from the MAP signal which is the output of the MAP amplifier unit 37. The determined parameter is proportional to the cardiac APD in the vicinity of the location at which the MAP signal is sensed.

The MAP amplifier unit 37 senses the MAP signal at the cardiac tissue. Optionally, but not necessarily, the MAP amplifier unit 37 may apply MAP inducing signals to the cardiac tissue, such as electrostatic induction electrical signals, electroporating current signals, or other MAP inducing signals, as is disclosed in detail in the above referenced U.S. Pat. No. 6,152,882 to Prutchi. If Map inducing signals need to be applied to the heart for MAP sensing, the microprocessor unit 35 may be operatively connected to the MAP amplifier unit 37 (connection not shown) for controlling the timing of application of the MAP inducing signals. If no chronic MAP recording is required, such as when the device 32D is used for short time periods only, the MAP amplifier unit may be of the type which perform sensing only such as MAP devices using the contact electrode method of Franz or any other devices using any other suitable short term MAP recording method known in the art.

The value of the parameter proportional to the APD is output to a controller or microprocessor 35 for processing. The microprocessor 35 is connected to the ETC unit 36. The ETC unit 36 is controlled by control signals generated by the microprocessor 35 of the APD determining unit 31D. The microprocessor 35 uses the value of the APD related parameter to compute the parameters of the ETC signal delivered to the heart. The computed ETC parameters may include the ETC signal starting time, the ETC signal duration, the ETC signal amplitude and the ETC signal waveform as is disclosed in detail hereinafter.

In the preferred embodiment illustrated in FIG. 3E, the device 32E includes an APD determining unit 31E and an ETC unit 36 capable of delivering ETC signals to the heart for controlling cardiac contractility. the APD determining unit 31E includes a MAP amplifier unit 37, a digitizing unit 39 connected thereto and a microprocessor unit 35 connected to the digitizing unit 39 and to the ETC unit 36. The MAP amplifier unit 37 operates to sense and amplify a MAP signal in or about the heart as disclosed for the MAP amplifier unit 37 of FIG. 3D. If Map inducing signals need to be applied to the heart for MAP sensing, the microprocessor unit 35 may be operatively connected to the MAP amplifier unit 37 to provide control signals for controlling the timing of application of the MAP inducing signals by the MAP amplifier unit 37. The amplified MAP signal is sent as output to the digitizing unit 39 for digitizing. The digitized MAP signal is sent to the microprocessor unit 35 which processes the digitized MAP signal and determines a parameter proportional to the cardiac APD (an estimated APD) in the vicinity of the location at which the MAP signal is sensed as is disclosed in detail hereinabove (FIG. 2A). The microprocessor 35 uses the value of the APD related parameter to compute the parameters of the ETC signal delivered to the heart. The computed ETC signal parameters may include the ETC signal starting time, the ETC signal duration, the ETC signal amplitude and the ETC signal waveform as is disclosed in detail hereinafter.

It is noted that, for the sake of clarity of illustration, FIGS. 3A–3E do not show the power source which energizes the various electrical components of the devices 32A–32E. However, as will be appreciated by those skilled in the art, the devices 32A–32E also include a power source (not shown), and may also include other various parts such as a memory unit (not shown) connected to the processor unit 35 for storing and retrieving data, and one or more timer units (not shown) connected to the processor unit 35 for providing clock signals for various timing functions. If any of the devices 32A–32E is an implantable device, the device may also include a telemetry unit (not shown) for communicating with a telemetry transceiver (not shown) external to the patient as is known in the art.

It is further noted that any of the devices 32A–32E may also be adapted to include pacing circuitry (not shown) including sensing and pacing units (not shown) for sensing and pacing one or more chambers of the heart as is known in the art.

It is still further noted that, in operation, each of the devices 32A–32E is connected to a plurality of electrodes (not shown in FIGS. 3A–3E) for performing MAP or CBE sensing (depending on the device type), for delivering ETC signals to the heart, and if the device has pacing capabilities, for performing sensing and pacing of the heart. In the devices performing MAP sensing, the MAP sensing electrodes may be any of the MAP sensing electrodes disclosed in the above referenced U.S. Pat. No. 6,152,882 to D. Prutchi. In the devices performing CBE sensing, the CBE sensing electrodes may be any of the CBE sensor electrodes used for close bipolar electrogram recording as disclosed in U.S. patent application Ser. No. 09/280,486, to Yuval Mika et al.

It will be appreciated by those skilled in the art that the APD determining circuits 34 and 38 of FIGS. 3B and 3D, respectively, may be implemented as analog or as digital circuits, or as hybrid digital/analog circuits. The details of other possible implementations of the devices 32B–32E are disclosed hereinafter.

Figure 4:
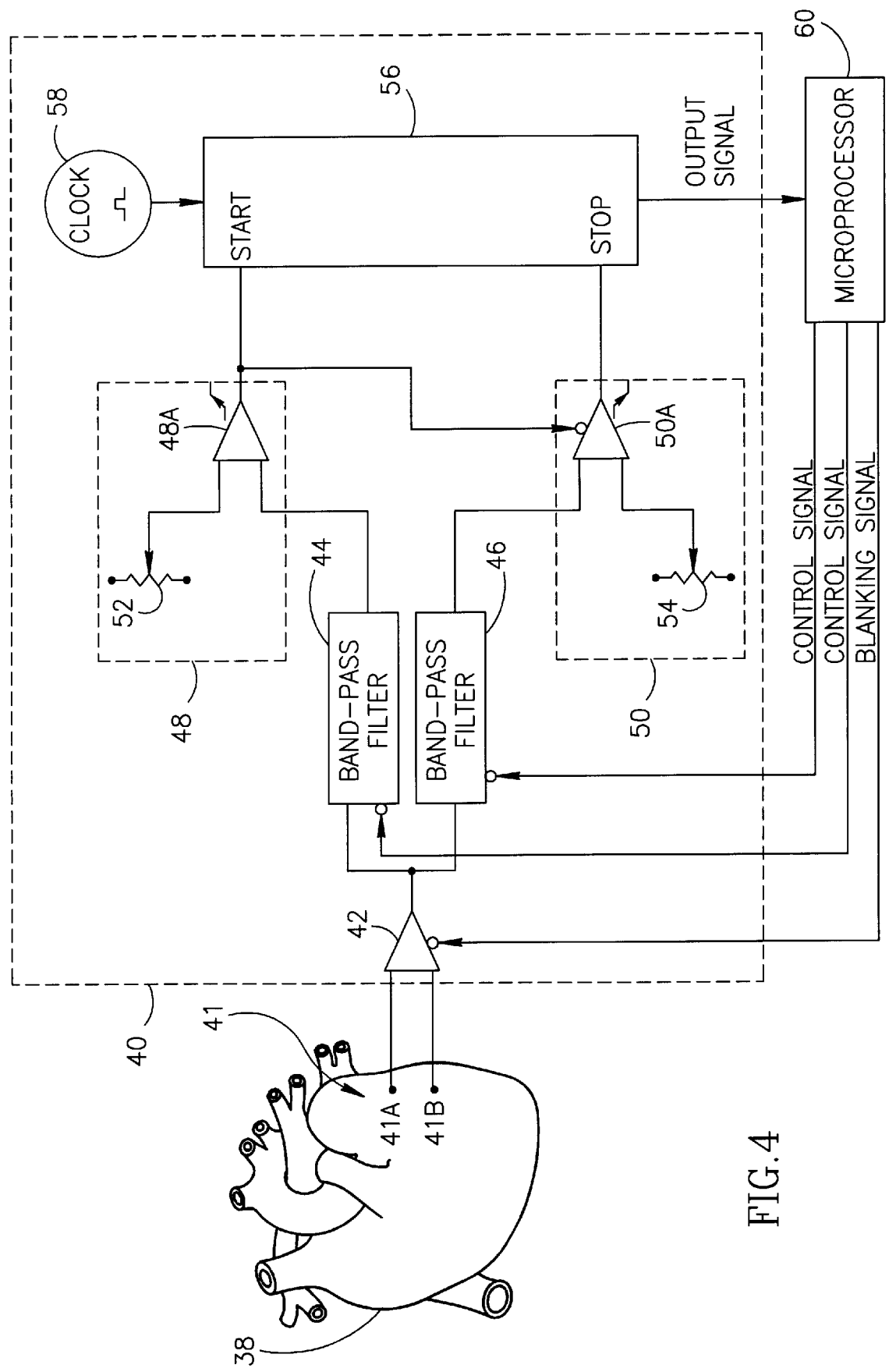
FIG. 4 is a schematic diagram illustrating circuitry for estimating the action potential duration from a close-bipolar electrogram signal, in accordance with a preferred embodiment of the present invention.

The circuitry 40 of FIG. 4 is suitably connected to a close-bipolar electrogram sensor 41 implanted in the heart 38. The close-bipolar sensor 41 includes two closely spaced apart electrodes 41A and 41B constructed and operative to obtain a CBE signal. The details of construction of CBE sensors and of the close-bipolar electrodes thereof are disclosed in detail in U.S. patent application Ser. No. 09/280,486, to Mika et al., referenced hereinabove, are not the subject matter of the present invention and are not further discussed in detail hereinafter.

Preferably, the electrodes 41A and 41B of the close-bipolar sensor 41 are disposed in the same lead (not shown in FIG. 4) which also includes the electrodes (not shown) which are used for delivering the ETC signal to the cardiac tissue. This ensures that the CBE signal is recorded from the same tissue portion to which the ETC signal is to be delivered or from the region of cardiac tissue which is affected by the delivered ETC signals. However, the electrodes 41A and 41B of the close-bipolar sensor 41 may also be disposed in a lead (not shown) which is separate from the lead including the ETC delivery electrodes (not shown). In the latter case, since the APD estimate obtained from the CBE signal is used to control the parameters of the ETC signal delivery, it is still preferred to position the bipolar sensor 41 close to the site to which the ETC signals are delivered, or close to the site which is affected by the delivered ETC signals.

The electrodes 41A and 41B are electrically connected to a differential amplifier 42. The output of the differential amplifier 42 is fed to a first bandpass filter 44 and to a second bandpass filter 46.

The first bandpass filter 44 has frequency response characteristics which selectively pass the spectral components of part 30B of the first component 30A of the CBE signal 30 (FIG. 2B) representing the differentiated fast upstroke of the fast depolarization, while attenuating the lower frequency spectral components of the second component 30E of the CBE signal of FIG. 2B. The filtered signal output is then fed to a tunable threshold circuit 48. The threshold circuit 48 includes a threshold unit 48A and a threshold setting potentiometer 52. The threshold unit 48A is suitably connected to the threshold setting potentiometer 52 which is used for threshold setting. The threshold circuit 48 may be implemented in various ways which are well known in the art and are therefore not disclosed in detail hereinafter. Preferably, the threshold circuit 48 is implemented as a slope detecting threshold circuit which also detects the slope of the input signal and triggers an output signal for an input signal having a voltage equal to or greater than the threshold voltage set on potentiometer 52, and having a positive slope, or having a slope which is within a specified range of slope values.

The output of the threshold circuit 48 is suitably connected to the start terminal of an edge activated binary counter 56 to determine the time at which threshold crossing occurred at the threshold circuit 48. The output of the threshold circuit 48 is also fed as a control signal to a threshold circuit 50. When the threshold circuit 48 outputs a signal indicating the detection of a threshold crossing, the output signal activates the threshold circuit 50 to start sensing.

The second bandpass filter 46 has frequency response characteristics which selectively pass the spectral components of the second component 30E of the CBE signal 30 (FIG. 2B) representing the differentiated fast repolarization of the local cardiac action potential, while attenuating the higher frequency spectral components of the first component 30A of the CBE signal of FIG. 2B. The filtered signal output is then fed to the second tunable threshold circuit 50. The threshold circuit 50 includes a threshold unit 50A and a threshold setting potentiometer 54. The threshold unit 50A is suitably connected to a threshold setting potentiometer 54 which is used for threshold setting. Preferably, the threshold circuit 50 also detects the slope of the input signal and triggers an output signal for an input signal having a voltage equal to or greater than the threshold voltage set on potentiometer 54, and having a negative slope, or having a slope which is within a specified range of slope values.

The output of the threshold circuit 50 is suitably connected to the stop terminal of the edge activated binary counter 56 to determine the time at which threshold crossing was detected by the threshold circuit 50. If desired, the threshold circuit 50 may be further controlled by the binary counter 56 or by a microprocessor 60 for inactivating the threshold circuit 50 after a stop signal was output from the threshold circuit 50. This control function may be implemented by suitably connecting a control output terminal (not shown) of the binary counter 56 or of the microprocessor 60, to a suitable disabling terminal (not shown) of the threshold circuit 50.

The edge activated binary counter 56 is suitably connected to a clock 58 which provides clock signals thereto. The edge activated binary counter 56 is also suitably connected to the microprocessor or controller 60 which is part of an ETC device (not shown in FIG. 4 for the sake of clarity of illustration) or a pacemaker/ETC device (not shown) and provides the microprocessor 60 with the value of a parameter representing the time elapsed between the detection of a threshold crossing by the first threshold circuit 48 and the detection of a threshold crossing by the second threshold circuit 50. Thus, a timer function is used to measure the value of a parameter which is closely related to the APD and which may be used as an estimated APD by the microprocessor 60. For example, the first threshold level of the threshold circuit 48 may be set to a value which is 50% of the averaged amplitude (taken over a plurality of beat cycles) of the positive peak of the first component 30A of FIG. 2B, and the second threshold value of the second threshold circuit 50 may be set to a value which is 50% of the averaged amplitude (taken over the same plurality of beat cycles) of the negative peak of the second component 30E of FIG. 2B. When such threshold values are used, the parameter which is output to the microprocessor 60 by the edge activated binary counter 56 is the value of the interval $\alpha T$ of FIG. 2B. As disclosed hereinabove, other threshold values, different than 50% of the negative and the positive peaks, may also be used to obtain a parameter related to the APD.

In accordance with another preferred embodiment of the present invention, the first threshold level of the threshold circuit 48 may be set to the value of the threshold level L1 of FIG. 2B and the value of the slope or slope range of the threshold circuit 48 (if a slope or slope detection criterion is being used) is set to a specified slope value or a specified slope range. The second threshold value of the second threshold circuit 50 may be set to the value of the threshold level L2 of FIG. 2B and the value of the slope or slope range of the second threshold circuit 50 (if a slope or slope detection criterion is being used) is set to a specified slope value or a specified slope range.

The value of the first and second threshold values (or of the threshold levels L1 and L2) and of any slope or slope range values (if slope criteria are being used) may be initially manually set by the physician after implantation of the electrodes 41A and 41B. However, in accordance with another preferred embodiment of the present invention, an equivalent of the circuitry 40 of FIG. 4 may be used by a software implementation in which the CBE signal is digitized by an analog to digital converter (not shown) and is fed to the microprocessor 60 and a software program embedded in the microprocessor 60 performs the computation of the value of the parameter related to the APD. If such an embodiment is used, the program embedded in the microprocessor 60 may periodically update the values of the thresholds based on averaged positive and negative peak values which are automatically computed from stored data of these peak values measured in CBE signals in a predetermined number of beat cycles preceding the current beat cycle. In a non-limiting example, the program may dynamically update the mean of the positive and negative peak values based on averaging the peak values determined in the four beat cycles preceding the current beat cycle. However, other numbers of beat cycles may be used, provided that the number of beat cycles used for the averaging is not too large such as will result in excessive masking of fast changes in the CBE signal peaks. This feature has the advantage of compensating for possible gradual changes in the CBE signal amplitude which may be caused by CBE sensor movements or other factors.

It is noted that the microprocessor 60 of FIG. 4 is optionally suitably connected to the differential amplifier 42 and to the first bandpass filter 44 and the second bandpass filter 46 to provide suitable blanking and/or control signals thereto. For example, the differential amplifier 42 may be blanked during the delivery of the ETC signal to the heart. The microprocessor 60 may also (optionally) send control signals to the first bandpass filter 44 or the second bandpass filter 46 or both to modify the frequency response characteristics of the first bandpass filter 44 or the second bandpass filter 46 or to modify the frequency response characteristics of both of the bandpass filters 44 and 46. The modification of the frequency response characteristics of any of the bandpass filters 44 and 46 may be manually performed following the physician input during a period of testing after the implantation of the electrodes in the patient or may be periodically or intermittently performed during checkup periods of the patient.

It is noted that at least some of the CBE signals and the MAP signals recorded in the heart in the presence of delivered ETC signals may include electrical artifacts resulting from the relatively high amplitude currents delivered as ETC signals to the cardiac tissue. Such artifacts may interfere with the determination of the APD related parameter disclosed hereinabove.

Figure 5A:
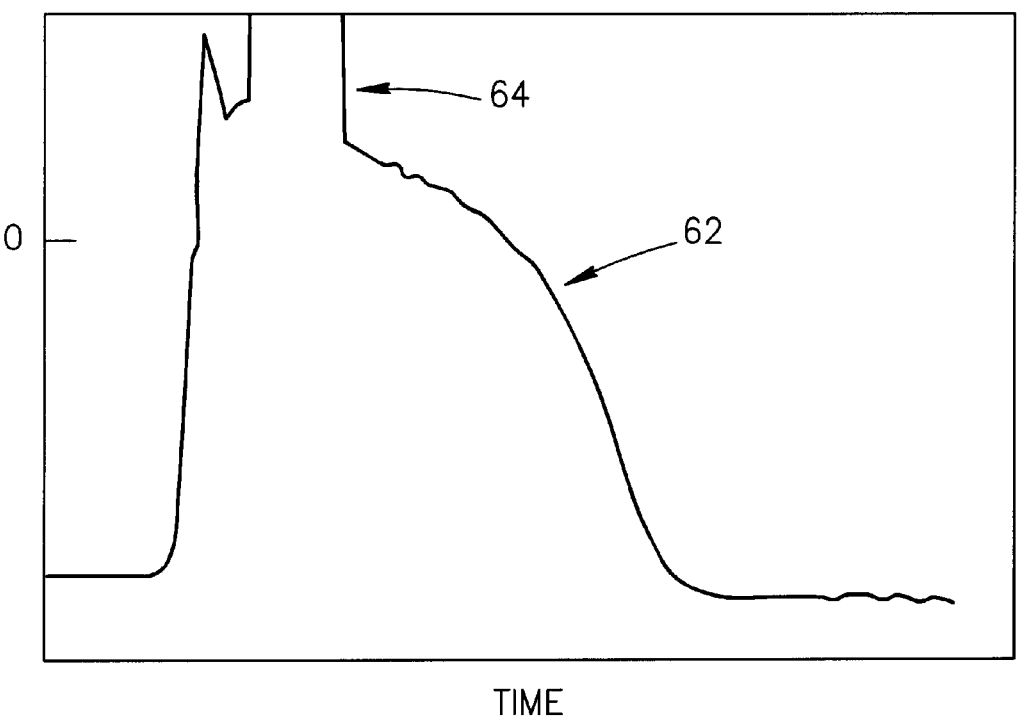
FIG. 5A is a diagram schematically illustrating an ETC signal induced artifact in a cardiac MAP signal.
Figure 5B:
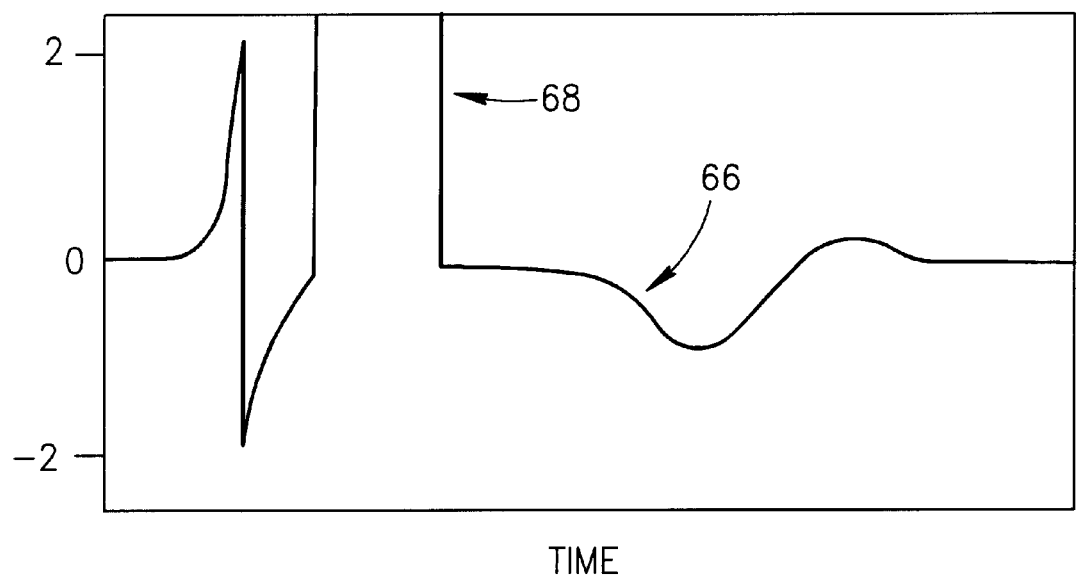
FIG. 5B is a diagram schematically illustrating an ETC signal induced artifact in a cardiac close-bipolar electrogram signal.

Reference is now briefly made to FIGS. 5A and 5B. FIG. 5A is a schematic diagram illustrating an ETC signal induced artifact in a cardiac MAP signal. FIG. 5B is a schematic diagram illustrating an ETC signal induced artifact in a cardiac close-bipolar electrogram signal. In FIG. 5A the vertical axis represents signal amplitude in arbitrary units and the horizontal axis represents time in arbitrary units. The curve 62 represents the recorded MAP signal. The large deflection 64 in the curve 62 represents an ETC signal induced electrical artifact, such artifacts may typically cause signal clipping in the amplifier units used in the sensing circuit. Typically, the duration of the MAP signal is approximately 150–300 milliseconds and the duration of the ETC induced artifact may be approximately 10–100 milliseconds.

In FIG. 5B the vertical axis represents signal amplitude in arbitrary units and the horizontal axis represents time in arbitrary units. The curve 66 represents the recorded CBE signal. The large deflection 68 in the curve 66 represents an ETC signal induced artifact, such artifacts may typically cause signal clipping in the amplifier units used in the sensing circuit.

In order to solve this electrical artifact problem the circuitry for determining the parameter proportional to the APD may have to be adapted as disclosed in detail hereinafter. Another possible approach is to determine the APD related parameter only for beat cycles during which an ETC signal was not delivered to the heart. This approach may be used is situations in which ETC signals are not applied in every beat cycle but are applied intermittently, such as, for example, every other beat cycle, or even at a lower frequency. Alternatively, such a method may be used by omitting the delivery of ETC signal in one beat cycle after a certain number of consecutive beat cycles during which ETC signals were delivered in every beat cycle, and using the value of the APD related parameter determined in this artifact-free beat cycle for determining the ETC delivery parameters until the next artifact free beat cycle is encountered. The timing of the "ETC free" beat cycle is controlled by the microprocessor controlling the ETC unit of the ETC device which also activates the circuitry for determining the APD related parameter only in those ETC free beat cycles to reduce power consumption.

Another solution to the artifact problem is to use various signal blanking methods as is known in the art. The blanking methods may be used for analog or combined analog/digital circuit implementations as disclosed hereinafter.

Yet another solution to the artifact problem may be to use digital methods which directly digitize the sensed CBE signal or the sensed MAP signal and process the digitized signals to eliminate or ignore the data points in the artifact related portion of the digitized signal. Such methods may also make use of interpolation methods to interpolate values for replacing the eliminated data points as is known in the art.

Preferably, the ignoring or eliminating the electrical artifact related portion of the digitized signal or for interpolating values for values for replacing the eliminated data points, are performed by the microprocessor unit 35 (FIGS. 3C and 3E). The timing data required for correctly identifying the data points including the electrical ETC related artifacts is available to the microprocessor 35, since the timing of the application of ETC signals to the heart by the ETC unit 36 is controlled by the microprocessor 35.

Figure 6:
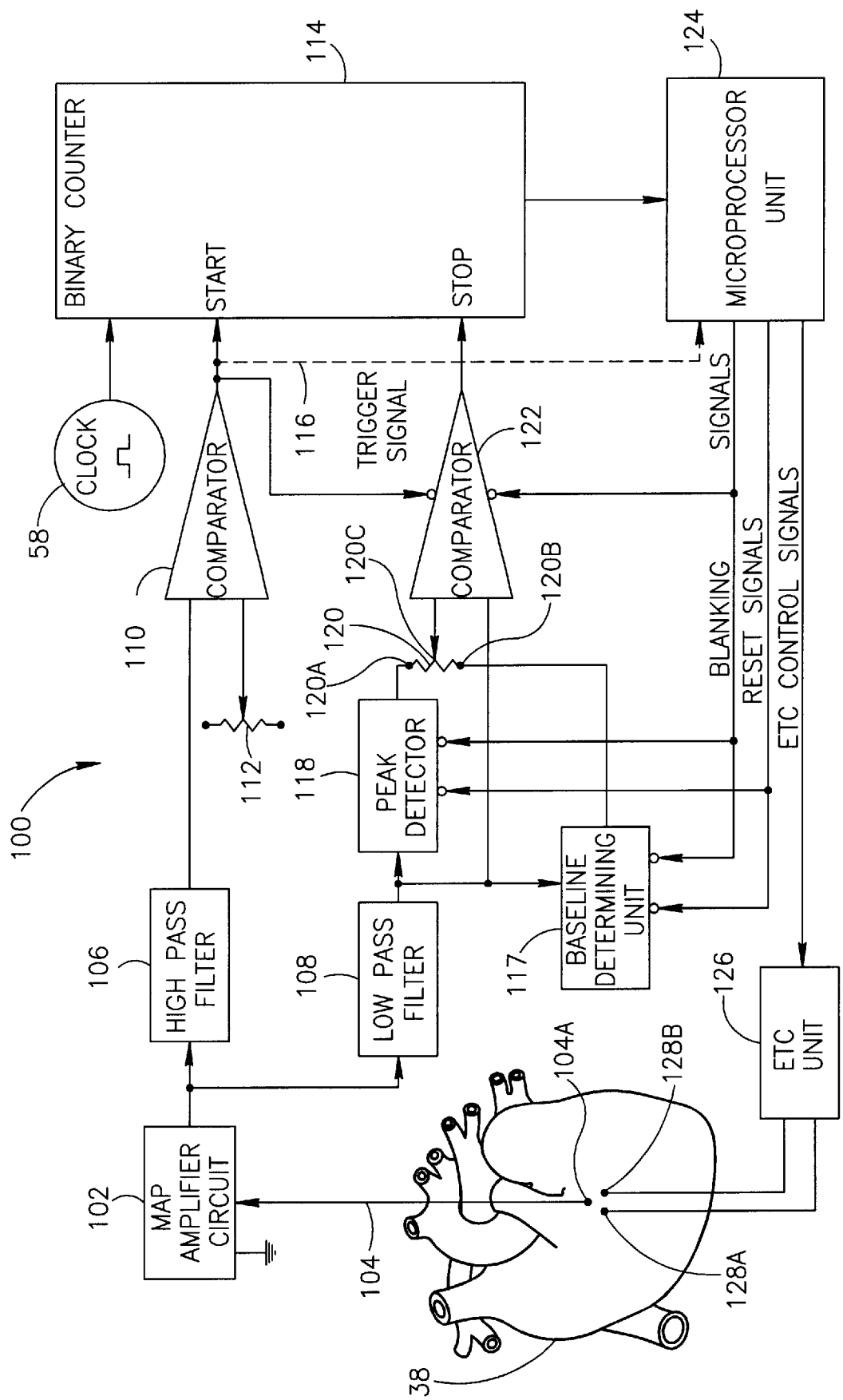
FIG. 6 is a schematic functional block diagram illustrating circuitry for estimating the action potential duration from a cardiac monophasic action potential signal, in accordance with a preferred embodiment of the present invention.

Reference is now made to FIG. 6 which is a schematic functional block diagram illustrating circuitry for estimating the action potential duration from a cardiac monophasic action potential signal, in accordance with a preferred embodiment of the present invention.

The circuitry 100 of FIG. 6 includes a MAP amplifier circuit 102. The MAP amplifier circuit 102 may be adapted for performing acute MAP recording as is known in the art. For example, circuitry adapted for the contact electrode method of Franz may be used. Alternatively, the MAP amplifier circuit 102 may be implemented as any of the circuits disclosed in the above referenced U.S. Pat. No. 6,152,882 to D. Prutchi, for performing chronic MAP recording as is known in the art. For example, the MAP amplifier circuit 102 may be adapted for using the electroporation MAP method, the electrostatic MAP method, the thermal MAP induction method using resistive tissue heating or direct RF tissue heating, or any other circuitry using any other methods for chronic MAP recording disclosed by Prutchi in U.S. Pat. No. 6,152,882.

The MAP amplifier circuit 102 is connected to a lead 104 including an electrode 104A disposed in or about a chamber of the heart, and adapted for MAP recording at or about the heart, preferably in or about the left ventricle of the heart. However, two or more electrodes (not shown) may be used which are adapted for MAP recording at or about the heart. For example, any of the electrode(s) or electrode configurations disclosed in the above referenced U.S. Pat. No. 6,152,882 to D. Prutchi, may be used in the present invention.

The MAP signal at the output of the MAP amplifier circuit 102 is simultaneously fed to a high-pass filter 106 connected to the MAP amplifier circuit 102 and to a low-pass filter 108 connected to the MAP amplifier circuit 102. The high pass filter 106 is suitably connected to one input terminal of a comparator 110. The second input terminal of the comparator 110 is connected to a potentiometer 112 for setting a reference voltage level. The output terminal of the comparator 110 is suitably connected to a start terminal of a binary counter 114. The binary counter 114 receives suitable clocking pulses from a clock 58 connected thereto. The high-pass filter 106 passes the high frequency content of the sharp leading edge 10B (of FIG. 2A) of the MAP signal but filters out any slow frequency components due to baseline shifts, drift or the like. When the amplitude of the voltage signal at the terminal of the comparator 110 connected to the high pass filter 106, is equal to the voltage value at the terminal of the comparator 110 connected to the potentiometer 112, the comparator 110 outputs a suitable control pulse to the start terminal of the binary counter 114. This control signal starts the binary counter 114 and may be, optionally, used as a trigger signal for initiating the delayed delivery of the ETC signal when such an ETC signal is required (this function is represented by the dashed line 116 labeled "trigger signal".

The low pass filter 108 is connected to a peak detector 118. The output terminal of the peak detector 118 is connected to the fixed terminal 120A of a voltage dividing potentiometer 120. The variable (adjustable) terminal 120C of the potentiometer 120 is suitably connected to an input terminal of a comparator 122 as illustrated. The output terminal of the low pass filter 108 is also connected to the second terminal of the comparator 122. The output terminal of the low pass filter 108 is also connected to a baseline determining unit 117 adapted to hold a voltage level representative of the MAP signal's baseline voltage level at its output as disclosed in detail hereinafter. The output terminal of the baseline determining unit 117 is connected to the second fixed terminal 120B of the voltage dividing potentiometer 120. The baseline determining unit 117 may be also (optionally) suitably connected to a microprocessor 124, to receive blanking and/or resetting control signals therefrom.

The low pass filter 108 attenuates the high frequency components of the MAP signal provided by the Map amplifier circuit 102 and selectively passes the low frequency components with little amplitude attenuation. Therefore, the low frequency parts of the MAP signal such as the MAP signal parts schematically represented by the region of the curve about the point 11 (FIG. 2A) representing the peak amplitude of the MAP plateau region, and the portions of the curve 10A (FIG. 2A) representing the fast repolarization phase of the MAP signal, are passed relatively unattenuated, while other high frequency components of the signal are strongly attenuated. The peak detector 118 determines the value of the peak amplitude of the low pass filtered MAP signal which is approximately equivalent to the point 11 (FIG. 2A).

The peak amplitude of the MAP signal is determined relative to the MAP baseline value represented by the signal part 10C (FIG. 2A) preceding the fast depolarization part 10B of the curve 10 (FIG. 2A).

The peak detector 118 holds the determined low pass filtered MAP peak amplitude value at its output until it is reset. Any high frequency components preceding the MAP peak amplitude of point 11, are attenuated in the low pass filtered MAP signal and therefore do not interfere with the determination and holding of the MAP peak amplitude value by the peak detector 118. The variable (adjustable) terminal 120C of the potentiometer 120 may be preset to a certain value which is a fraction of the value of the MAP peak amplitude value.

Since the baseline of the MAP signal is not necessarily at a zero potential level, and may drift or shift in time, the second fixed terminal 120B of the potentiometer 120 is connected to the output terminal of the baseline determining unit 117. The baseline determining unit 117 outputs a voltage level representative of the MAP baseline voltage level. Thus the voltage difference across the fixed terminals 120A and 120B of the potentiometer 120, represents the voltage difference between the baseline of the MAP signal (which approximates the MAP baseline value of the part 10C of FIG. 2A) and the MAP peak amplitude value (represented by the point 11 of FIG. 2A). This arrangement has the advantage of providing a voltage value representing the MAP peak amplitude irrespective of baseline shifts. The baseline determining unit 117 may be implemented as a valley detector (minimum detector) circuit, which holds at its output terminal the minimal voltage value of a signal which is fed to its input terminal. However, the baseline determining unit 117 may be implemented as any other analog or digital circuit which is capable of determining and holding as its output a value representative of the baseline of the low pass filtered MAP signal. The construction and operation of such baseline determining units and valley detectors is well known in the art, is not the subject matter of the present invention and is therefor not disclosed in detail hereinafter.

the adjustment of the setting of the variable terminal 120C of the potentionmeter 120 is manually adjusted by the physician or the operator of the circuitry 100 during a test period performed after electrode implantation in the patient. The physician may check the MAP signal and adjust the setting of the variable terminal 120C of the potentiometer 120 to ensure proper determination of the estimated APD value according to the desired determination method. For example, if the $MAPD_{90}$ method of Franz is used, the physician adjusts the setting of the variable terminal 120C of the potentiometer 120 such that the voltage at the terminal of the comparator 122 which is connected to the variable terminal 120C of the potentiometer 120 is about 10% of the total voltage difference between the two fixed terminals 120A and 120B of the potentiometer 120. However, other settings may also be used if desired.

When the signal amplitude value at the terminal of the comparator 122 which is connected directly to the output of the low pass filter 108 is equal to the value of the voltage at the variable terminal 120C of the comparator 122 which is connected to the potentiometer 120, the comparator 122 outputs a suitable control signal to the stop terminal of the binary counter 114. This control signal stops the binary counter 114 from counting. The binary counter 114 outputs the count value representing the estimated APD duration to the microprocessor unit 124. The microprocessor unit 124 processes the value of the estimated APD, as is disclosed in detail hereinafter, for determining the parameters of the ETC signal to be delivered to the heart 38 by an ETC unit 126 connected to the microprocessor 124. The microprocessor 124 controls the ETC unit 126 using ETC control signals. The ETC unit 126 is suitably connected to a pair of electrodes 128A and 128B for delivering ETC signals to the heart 38 as is known in the art. Preferably, the ETC delivering electrodes 128A and 128B are disposed close to the cardiac site to which the electrode 104A is applied, as is disclosed in detail hereinafter.

In accordance with one non-limiting example, when the voltage dividing potentiometer 120 is set such that the voltage at the terminal of the comparator 122 is 10% of the voltage held at the output terminal of the peak detector 118, the value of the APD related parameter which is output by the binary counter 114 represents the $MAPD_{90}$ value disclosed hereinabove and illustrated in FIG. 2A. However, the potentiometer 120 may be set at other settings to provide other APD related parameters. The precise setting of the potentiometer 120 may depend, inter alia, on the particular, patient specific, MAP signal parameters such as the mean peak MAP amplitude, the signal to noise ratio of the MAP signal and other factors.

After the APD related parameter value is received by the microprocessor 124, the microprocessor 124 outputs a reset signal to the peak detector 118 for resetting the peak detector 118 in order to ready the peak detector 118 for detecting and holding the value of the low pass filtered peak amplitude of the MAP signal of the next cardiac beat cycle. The reset signals may also be used for resetting the baseline determining unit 117 as shown in FIG. 6.

When the MAP signal which is currently processed includes an ETC induced artifact such as for example the ETC induced artifact 64 of the MAP signal 62 of FIG. 5A, the ETC induced artifact may adversely interfere with the determination of the value of the APD related parameter, due to artifact amplitude, circuitry saturation, and other factors. To avoid such undesirable interference, the ETC induced artifact may have to be blanked. The blanking function may be performed by the microprocessor unit 124 which may (optionally) send blanking signals to the peak detector 118, the baseline determining unit 117, and the comparator 122 based on the timing of the ETC signal which is to be delivered to the cardiac tissue. The microprocessor 124 may deliver these blanking signals in synchrony with the ETC control signals which control the timing of delivery of ETC signal by the ETC unit 126 in such a manner that the entire ETC induced artifact is properly blanked.

It will be appreciated by those skilled in the art that, while in the preferred embodiment illustrated in FIG. 6, parts of the circuitry 100 for determining the value of the APD related parameter use an analog implementation, other preferred embodiments such as the preferred embodiment illustrated in FIG. 3E may use digital implementations of the circuitry 100 which are within the scope of the present invention. In this preferred embodiment, all the filtering, peak detection, and comparator functions are digitally implemented by a software program operative on the microprocessor 35 (FIG. 3E). In such a preferred embodiment, the ETC induced artifact elimination may be performed by simply ignoring the digital data points which include the artifact signal based on the timing data of the ETC delivery available to the microprocessor 35 (FIG. 3E). Alternatively, the microprocessor 35 may use other methods for removing the ETC induced artifact, such as, for example, by digitally subtracting from the MAP signal a signal which is similar to the average waveform of the ETC induced artifact. This average waveform signal may be obtained by measuring the average ETC induced artifact shape and amplitude in the same patient is an initial calibration or data acquisition period, or may be intermittently or periodically updated by automatically repeating such calibration or data acquisition periods to compensate for possible changes in tissue resistance with time which may lead to changes in the ETC induced artifact shape or amplitude. Such signal subtraction methods and automatic periodical data acquisition methods are well known in the art and are therefore not disclosed in detail hereinafter.

It is noted that, preferably, the MAP electrode(s) 104A and the ETC electrodes 128A and 128B are disposed close to each other such that the MAP signal is recorded from about the same tissue portion to which the ETC signals are delivered during ETC therapy. Thus, while the ETC electrodes 128A and 128B and the MAP electrode(s) 104A may be disposed in separate leads, preferably, in accordance with a preferred embodiment of the present invention, the ETC electrodes 128A and 128B and the MAP electrode(s) 104A are disposed in the same lead (not shown in FIG. 6). This has the advantage of reducing the number of required leads, decreasing patient risk and shortening and simplifying the procedures of electrode placement.

Control of ETC Parameters Using Estimated APD

As disclosed hereinabove, CBE sensing and MAP sensing may be used to obtain estimated APD values which are also referred to as APD related parameter values, throughout the present application.

The estimated APD values may be applied to control various ETC parameters for improving the safety and the effectiveness of ETC signal delivery.

Figure 7:
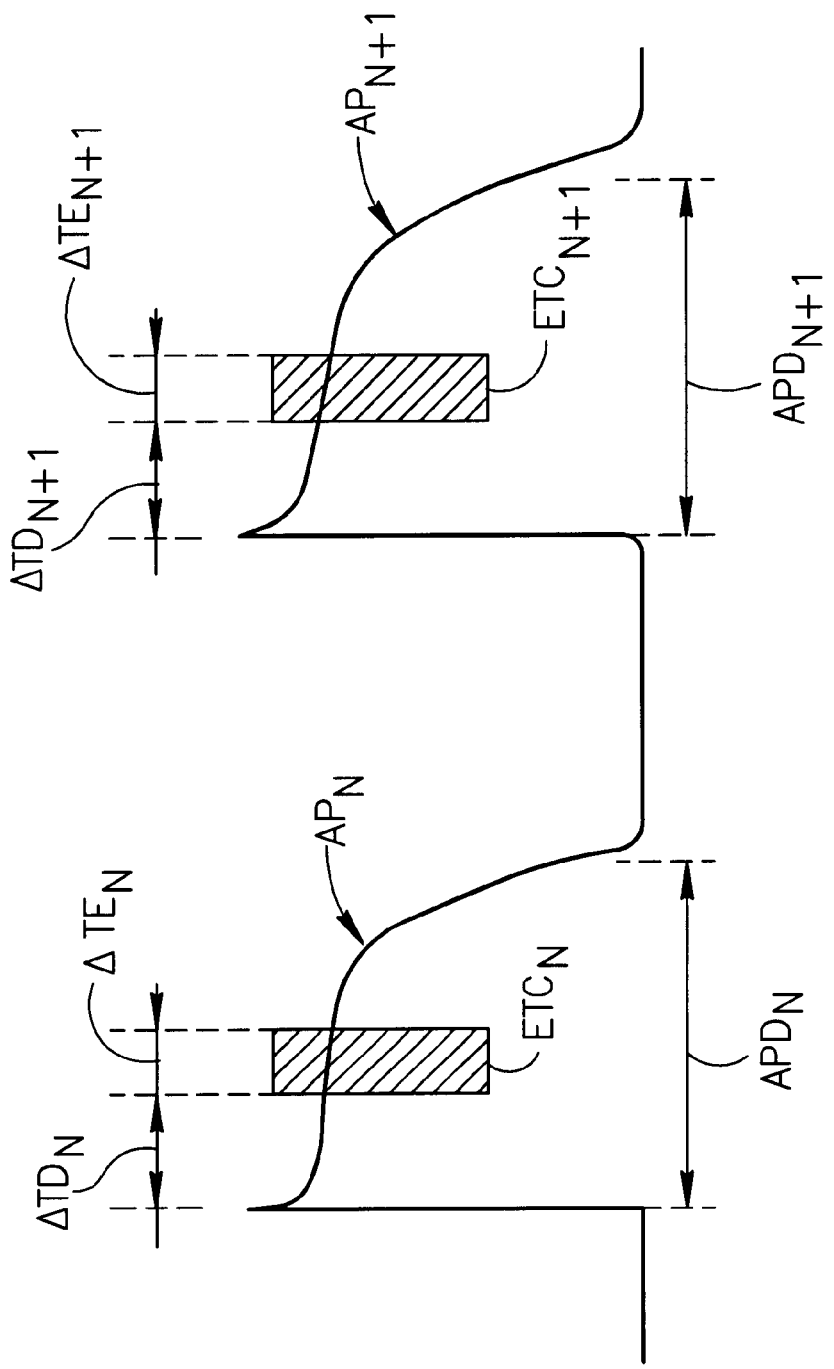
FIG. 7 is a schematic diagram useful in understanding the details of a method of controlling the ETC delivery parameters on a beat by beat basis using an estimated APD value, in accordance with a preferred embodiment of the present invention.

Reference is now made to FIG. 7 which is a schematic diagram useful in understanding the details of a method of controlling the ETC delivery parameters on a beat by beat basis using an estimated APD value, in accordance with a preferred embodiment of the present invention.

The curves labeled $AP_N$ and $AP_{N+1}$ schematically represent the time course of two consecutive cardiac action potentials. The hatched vertical bars labeled $ETC_N$ and $ETC_{N+1}$ schematically represent the positioning of ETC signals which are delivered to the heart within the plateau period of the action potentials $AP_N$ and $AP_{N+1}$, respectively. The time interval $\Delta TE_N$ represents the duration of the ETC signal $ETC_N$ and the time interval $\Delta TE_{N+1}$ represents the duration of the ETC signal $ETC_{N+1}$. The time interval $\Delta TD_N$ represents the ETC delay used for the action potential $AP_N$, and the time interval $\Delta TD_{N+1}$ represents the ETC delay used for the action potential $AP_{N+1}$. The time interval $APD_N$ represents the estimated APD determined for the action potential $AP_N$, and the time interval $APD_{N+1}$ represents the estimated APD determined for the action potential $AP_{N+1}$. It is noted that, the trigger for ETC delay time intervals $\Delta TD_N$ and $\Delta TD_{N+1}$ may be implemented using various detection methods. For example, when the MAP sensing method disclosed hereinabove is used for determining the estimated APD, in accordance with a preferred embodiment of the present invention, the ETC delay may be the interval between the time of detection of the sharp leading edge in part 10B representing the fast depolarization phase of the MAP signal curve 10 of FIG. 2A, and the time of starting the delivery of the ETC signal. In such a case, the estimated APD parameters $APD_N$ and $APD_{N+1}$ may be determined as described in detail in the method using MAP signals disclosed hereinabove and illustrated in FIG. 2A. For example, the estimated APD parameters $APD_N$ and $APD_{N+1}$ may be the $MAPD_{90}$ of FIG. 2A. However, other estimated APD parameters, such as $MAPD_{80}$, $MAPD_{70}$ disclosed hereinabove, or any other suitable APD parameters may also be used.

Alternatively, in accordance with another preferred embodiment of the present invention, the CBE signal method may be used for determining the estimated APD as disclosed hereinabove and illustrated in FIG. 2B. In this embodiment, the ETC delay may be the interval between the time of detection T1 (FIG. 2B) of the 50% maximum amplitude of the first component 30A (FIG. 2B) and the time of starting the delivery of the ETC signal. The estimated APD of $APD_N$ and $APD_{N+1}$ is determined as the time interval $\Delta T$ of FIG. 2B. For example, the 50% maximum amplitude of the first component 30A and the 50% minimum amplitude of the second component 30E may be used. However, various other suitable combinations may be used such as for example a 40% maximum amplitude of the first component 30A and a 60% minimum amplitude of the second component 30E may be used for computing $\Delta T$.

Additionally, when the method of determining the estimated APD value is based on the method disclosed hereinabove for determining the time interval $\Delta T$ using detection criteria based on crossing of specified threshold levels such as, but not limited to, the threshold levels L1 and L2 (of FIG. 2B) with or without the additional detection criteria such as slopes values or slope value ranges as disclosed hereinabove, the estimated APD of $APD_N$ and $APD_{N+1}$ is determined as the time interval $\Delta T$ of FIG. 2B determined using the specified threshold level or threshold level and slope combinations as disclosed hereinabove. The level/slope method may be used to reduce the probability of false positive signal component detection which may lead to an error in the determined value of $\Delta T$. This reduction may be achieved through empirical optimizing of the threshold levels and (optionally) the slope or slope range values which may be individually performed for each patient to account for variations in electrode positioning, signal to noise ratio and other patient specific conditions.

In accordance with a preferred embodiment of the present invention, the parameters $\Delta TD_{N+1}$ and $\Delta TE_{N+1}$ of the ETC signal $ETC_{N+1}$ are determined from the values of the parameter $APD_N$ estimated for the action potential $AP_N$ immediately preceding the action potential $AP_{N+1}$. Since the values of the ETC signal delay and the ETC signal duration may be made to change proportionally to changes in the estimated APD of the preceding action potential, The following equations 1 and 2 may be used, $$\Delta TD_{N+1} = \alpha(APD_N) + C_1 \quad (1)$$

$$\Delta TE_{N+1} = \beta(APD_N) + C_2 \quad (2)$$

wherein $\alpha$ and $\beta$ and $C_1$ and $C_2$ are empirically determined constants.

Typically, as empirically determined from, for example, in-vitro and in-vivo experiments in laboratory animals (including dogs and pigs) and in preliminary clinical trials in humans, for cardiac action potentials having an average APD of approximately 180 milliseconds acceptable values of $\alpha$ are approximately in the range of $\alpha=0$–$0.6$ and acceptable values of $\beta$ are approximately in the range of $\beta=0$–$0.4$. Typically, in humans $C_1=30$ milliseconds and $C_2=20$ milliseconds. However, the above values of $\alpha$, $\beta$, $C_1$ and $C_2$ may change and may have to be empirically determined for each patient individually depending, inter alia, on the patient's APD value range. Thus, the above values of $\alpha$, $\beta$, $C_1$ and $C_2$ are given by way of a non-limiting example only and other values of $\alpha$ and $\beta$, $C_1$, and $C_2$ may also be used in the present invention, depending, inter alia, on the type of ETC waveform and amplitude which are used and on the patient's cardiac APD range.

After the values of $\alpha$, $\beta$, $C_1$ and $C_2$ are determined for a patient they may be set or programmed into the memory of the ETC device and are used as programmed with or without periodic recalibration during patient checkup sessions. Alternatively, the values of $\alpha$, $\beta$, $C_1$ and $C_2$ may be automatically modifiable by any of the microprocessors 35, 60, 124 and 348, based on heart rate data and/or on patient activity as determined by any suitable method known in the art.

It is noted that, while the methods disclosed herein, disclose the use of the estimated APD for determining the delay and duration parameters of the ETC signal, other preferred embodiments of the invention may also use the estimated APD value for modifying or controlling other parameters of the ETC signal. For example, one or more of the shape, polarity, waveform and amplitude of the ETC signal may be varied as a function of the estimated APD value. Since the safety and efficacy of the ETC signal may be affected by one or more of these parameters, modifying one or more of these parameters based on the estimated APD value may also improve the safety and/or the efficacy of the ETC therapy.

In accordance with one non-limiting example, the amplitude of the ETC signal may be modified based on the estimated APD value. For example, if the duration of an ETC signal, computed as disclosed hereinabove, is shortened based on the current estimated APD value in order to improve the safety of ETC signal application, the ETC signal efficacy may decrease. However, the amplitude of the same ETC signal may be increased (within certain practical limits) in order to improve the ETC signal efficacy which would have decreased due to the shorter exposure time of the tissue to the signal.

Figure 8:
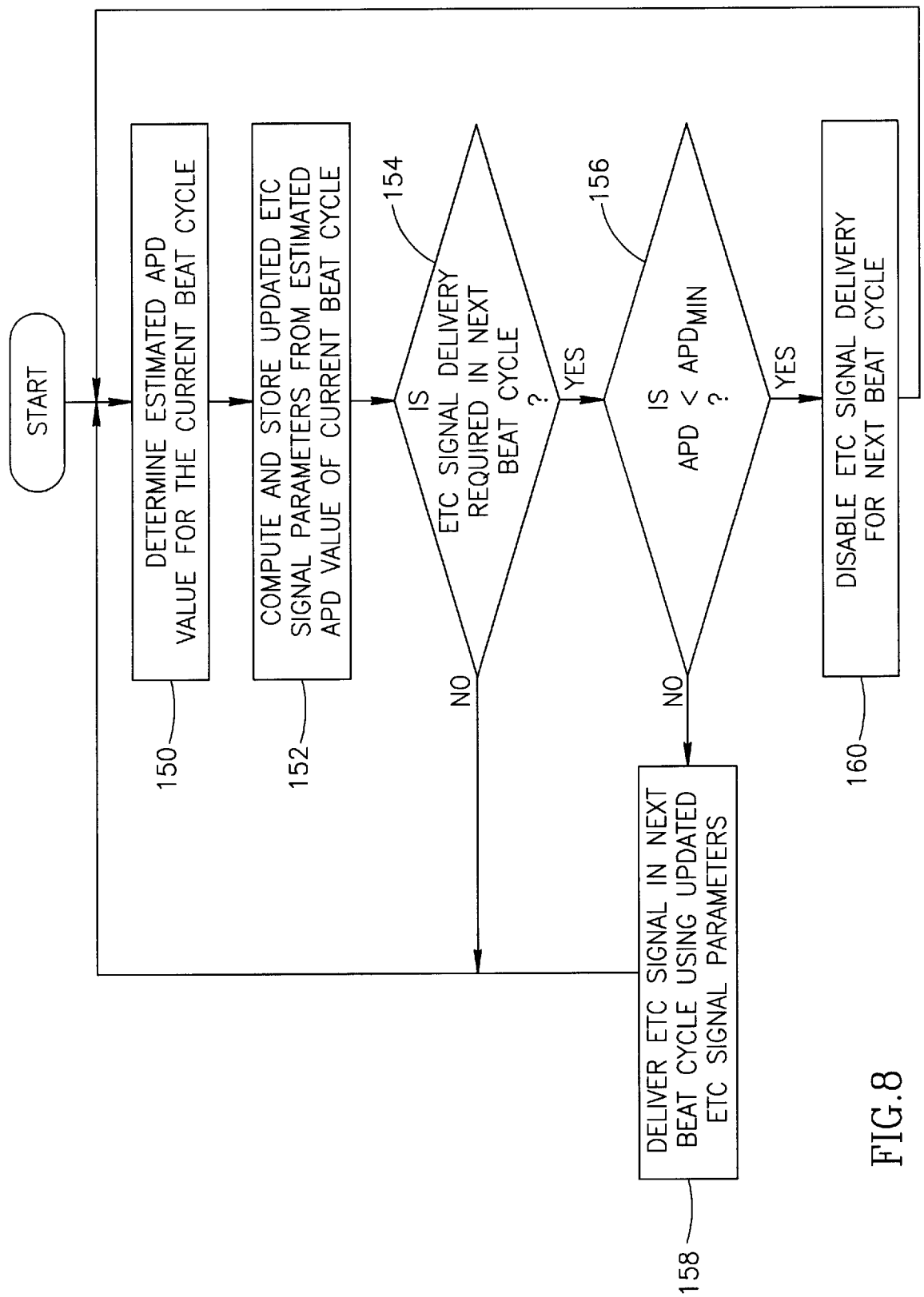
FIG. 8 is a schematic control flow diagram representing the steps of a method for controlling the parameters of ETC signals delivered to the heart using estimated action potential duration values.

Reference is now made to FIG. 8 which is a schematic control flow diagram representing the steps of a method for controlling the parameters of ETC signals delivered to the heart using estimated action potential duration values. The method may be applied in ETC devices or systems incorporating the devices 32A or 32B of FIGS. 3A and 3B, respectively, therewithin.

The method is typically implemented by a software program embedded in the microprocessor controlling the ETC signal delivery (such as, but not limited to, the microprocessor unit 35 of the devices 32A–32E, and the microprocessor units 60 and 124 of FIGS. 4 and 6, respectively). In operation, the program determines the estimated APD value for the current beat cycle (step 150). The estimated APD value may be obtained by using the CBE method or the MAP method as disclosed hereinabove. The program then computes the updated ETC signal parameters from the estimated APD value of the current beat cycle and stores the updated ETC parameters (step 152). The ETC signal parameters computed in step 152 may include the ETC delay and the ETC duration. The computation of the updated ETC parameters from the estimated APD value is performed as disclosed in equations 1 and 2 hereinabove. The updated ETC parameters may be stored in the memory (not shown) accessible to the microprocessor in which the program is embedded. The program then checks whether ETC signal delivery is required in the next beat cycle (step 154).

It is noted that, the data determining whether ETC signal delivery is scheduled for the next beat cycle is typically provided by a different program or programs embedded in the microprocessor and responsive to data obtained from sensor signals indicative of the cardiac and/or other metabolic or physiologic patient conditions, as is known in the art. However, such programs and sensors are not, by themselves, the subject matter of the present invention and are therefore not discussed in detail hereinafter.

If no ETC delivery is required (scheduled) for the next cardiac beat, the program returns control to step 150 to determine the estimated APD value for the next cardiac beat. If ETC delivery is required for the next cardiac beat, the program checks whether APD<$APD_{MIN}$ (step 156) wherein APD is the estimated APD value for the current beat cycle and $APD_{MIN}$ is the minimal acceptable action potential value.

The value of $APD_{MIN}$ may be a preset safety value which is manually set by a physician based on the physician's empirical determination of the shortest acceptable estimated APD duration following which an ETC signal may still be safely delivered to the patient's heart in the next beat cycle without endangering the patient. Typically, when ETC therapy is delivered, the APD value tends to gradually increase. However, under certain circumstances such as myocardial ischemia which is related or non-related to ETC signal delivery, the APD may be shortened. Under such conditions, it is advisable to stop ETC signal delivery for safety reasons. Thus, the safety value is implemented to detect the shortening and disable the delivery of ETC signals, until the APD value is equal to or larger than the value of $APD_{MIN}$.

If APD is larger than or equal to $APD_{MIN}$, the program delivers an ETC signal to the heart in the next beat cycle using the current updated ETC signal parameters (step 158) and returns control to step 150. If APD<$APD_{MIN}$, the program disables the delivery of an ETC signal in the next beat cycle (step 160), and returns control to step 150.

It is noted that, the method illustrated in FIG. 8 updates the ETC parameters on a beat by beat basis. However, as explained in detail above, the updated ETC parameters of an ETC signal delivered to the heart in a current beat cycle are computed from the estimated APD of the beat cycle preceding the current beat cycle. Thus, the method assumes that the action potential duration of a current beat is similar to, though it need not be identical with, the action potential duration of the beat preceding the current beat. Thus, the control of the ETC parameters is a predictive control type based on the result of a measurement performed in a prior cardiac beat cycle and is therefore referred to as a "near real-time control" herein.

It is further noted that, since the determination of estimated APD in the above method is performed for each beat cycle, the device using this method must be capable of performing the determination of the APD in the presence of the ETC signal induced artifact superimposed on the MAP or CBE signal as disclosed hereinabove. However, it may be desired to control the ETC signal parameters base on estimated APD in situations in which for practical or economical reasons, the circuitry available is not capable to satisfactorily perform the determination of the estimated APD in the presence of an ETC signal induced artifacts. This situation may be addressed by using a method which interrupts the delivery of ETC signals for enabling the performing of a measurement of the estimated APD.

Reference is now made to FIGS. 9–13 which are schematic graphs useful in understanding a method for controlling the ETC signal parameters by determining the estimated action potential duration during a time period in which ETC signal delivery is interrupted, in accordance with another preferred embodiment of the present invention.

FIG. 9 illustrates the time varying effects of ETC delivery on the end systolic pressure (ESP) and the end diastolic pressure (EDP) measured in the left ventricle of the heart. The curve 200 represents the left ventricular ESP envelope and the curve 202 represents the left ventricular EDP envelope. The vertical axis represents pressure amplitude in arbitrary units and the horizontal axis represents time in arbitrary units. The cross-hatched bars 204, 206 and 208 represent the duration of periods of delivering ETC signals to the heart (the actual ETC signals are not shown in FIG. 9) Typically, during the time periods represented by the cross-hatched bars 204, 206 and 208 trains of ETC signals are delivered to the heart. It is assumed for simplicity of presentation that the ETC signals are delivered continuously during the time periods represented by the cross-hatched bars 204, 206 and 208, such that one ETC signal is delivered to the heart within the duration of each cardiac action potential (not shown in FIG. 9).

The arrows labeled $T_0$, $T_1$, $T_2$ and $T_3$, represent selected time points along the time axis of FIG. 9. As illustrated, the application of ETC signal trains to the heart results in gradual increase of the ESP envelope which may stabilize at a certain value (depending, inter alia, on the train duration and on the ETC signal timing, amplitude and waveform parameters). The EDP envelope gradually decreases during the application of ETC signal trains to the heart. After the termination of the application of ETC signal trains to the heart, the ESP envelope gradually decreases while the EDP envelope gradually increases.

Each of FIGS. 10,11,12 and 13, schematically illustrates a single MAP signal recorded at a time point represented by the arrows $T_0$, $T_1$, $T_2$ and $T_3$, of FIG. 9, respectively. The vertical axis of each of the graphs of FIGS. 10–13 represents the MAP signal amplitude in arbitrary units, and the horizontal axis of each of the graphs of FIGS. 10–13 represents time in arbitrary units. It is noted that the time scale of FIGS. 10–13 is different than the time scale of FIG. 9.

Turning to FIG. 10, the curve labeled $MAP_0$ represents the cardiac MAP signal recorded at the time point indicated by the arrow $T_0$ of FIG. 9. The double headed arrow labeled $APD_0$ represents the estimated APD value determined for the MAP signal $MAP_0$ as disclosed in detail hereinabove. As can be seen in FIG. 9, the MAP signal $MAP_0$ is recorded at a time period preceding the time period 204 of ETC signal delivery. This time period serves as a baseline period for determining the estimated APD value at a time free of the effects of prior ETC therapy. Thus the value of $APD_0$ is used as a baseline value.

Turning to FIG. 11, the curve labeled $MAP_1$ represents a cardiac MAP signal recorded at the time point indicated by the arrow $T_1$ falling within the time period 204 of ETC signal delivery of FIG. 9. The double headed arrow labeled $APD_1$ represents the APD of the MAP signal $MAP_1$. The hatched bar labeled 210 represents the duration of the ETC signal delivered to the heart. It is noted that, the value of $APD_1$ is not computed during the duration of the time period 204 of delivering ETC signals and is only shown here for comparison purposes. As can be seen in FIGS. 10 and 11, the duration of the MAP signal $MAP_1$ is shortened relative to the duration of the MAP signal $MAP_0$, due to the delivery of ETC therapy. The ETC signal parameters for the ETC signal delivered within the beat cycle including the MAP signal $MAP_1$ are computed from the determined "baseline" value $APD_0$ by using the equations 1 and 2 disclosed hereinabove. Thus, the ETC signal delay $\Delta TD_1$ of the ETC signal 210 is computed as $\Delta TD_1 = \alpha(APD_0) + C_1$, and the ETC signal duration labeled $\Delta TE_1$ is computed as $\Delta TE_1 = \beta(APD_0) + C_2$.

Returning to FIG. 9, the period of ETC therapy delivery represented by the cross hatched bar 204 is terminated for enabling the determining of a new updated value of the estimated APD. Care is taken to ensure that the duration of therapy represented by the bar 204 is short enough such that the resulting changes in APD do not lead to a detrimental effect on the safety and efficacy of the ETC signal application, due to a shift of the ETC signal into the vulnerable period of the fast repolarization or due to the positioning of the ETC signal within an action potential phase which results in significant reduction in the desired ETC signal therapeutic effect.

This termination of the ETC therapy is used in the method to obtain another updated value of the estimated APD as disclosed hereinbelow.

Turning to FIG. 12, the curve labeled $MAP_2$ represents a cardiac MAP signal recorded at the time point indicated by the arrow $T_2$ (of FIG. 9) falling within the time period after the termination of ETC signal delivery. The double headed arrow labeled $APD_2$ represents the estimated APD value computed for the MAP signal $MAP_2$. It is noted that, the time $T_2$ of computing of the estimated APD value is selected to be close enough to the termination of the ETC therapy period 204, such that the estimated APD value obtained at time $T_2$ is not excessively changed and can therefore fairly accurately represent the approximate APD value that would have been measured at the end of the ETC therapy period 204 if it was possible to actually perform the measurement.

Thus, the new updated estimated APD value may now be used to compute the ETC signal parameters for use in the ETC Therapy time period which is represented by the cross hatched bar 206 of FIG. 9.

Turning to FIG. 13, the curve labeled $MAP_3$ represents a cardiac MAP signal recorded at the time point indicated by the arrow $T_3$ falling within the time period of ETC signal delivery 206 of FIG. 9. The hatched bar labeled 212 represents the duration of the ETC signal delivered to the heart. The ETC signal parameters for the ETC signal delivered within the beat cycle including the MAP signal $MAP_3$ are computed from the determined value $APD_2$ by using the equations 1 and 2 disclosed hereinabove.

Thus, the ETC signal delay $\Delta TD_3$ of the ETC signal 212 is computed as $\Delta TD_3 = \alpha(APD_2) + C_1$. The ETC signal duration of the ETC signal 212 is labeled $\Delta TE_3$, and is computed as $\Delta TE_3 = \beta(APD_2) + C_2$. Again, care is taken to ensure that the duration of therapy represented by the bar 206 is short enough such that the resulting changes in APD do not lead to a detrimental effect on the safety and efficacy of the ETC signal application, due to a shift of the ETC signal into the vulnerable period of the fast repolarization or towards an action potential phase which results in significant reduction in ETC signal desired therapeutic effect.

It is noted that, the allowable duration of the ETC Therapy periods such as the periods 204 and 206 may have to be empirically determined for each individual patient, and communicated telemetrically or non-telemetrically into the ETC device which is implementing the method of the present invention.

It is further noted that, while FIG. 9 shows a case in which the application of ETC therapy in the period 204 resulted in shortening of the APD, in which case the method proportionally shortens the delay and the duration of the ETC in the next ETC therapy period 206, typically, the application of ETC therapy to the heart results in lengthening of the APD which is associated with an increased contractility (positive inotropic effect). In these typical cases, the same equations 1 and 2 are used such that the delay and the duration of the ETC signal are increased proportionally to the increase in APD. This increase in the delay and duration of the ETC signal may increase the efficacy of the ETC therapy without substantially decreasing the safety of ETC therapy since the ETC signal is not delivered closer to the vulnerable fast repolarization period due to the overall increase in the APD duration.

Figure 14A:
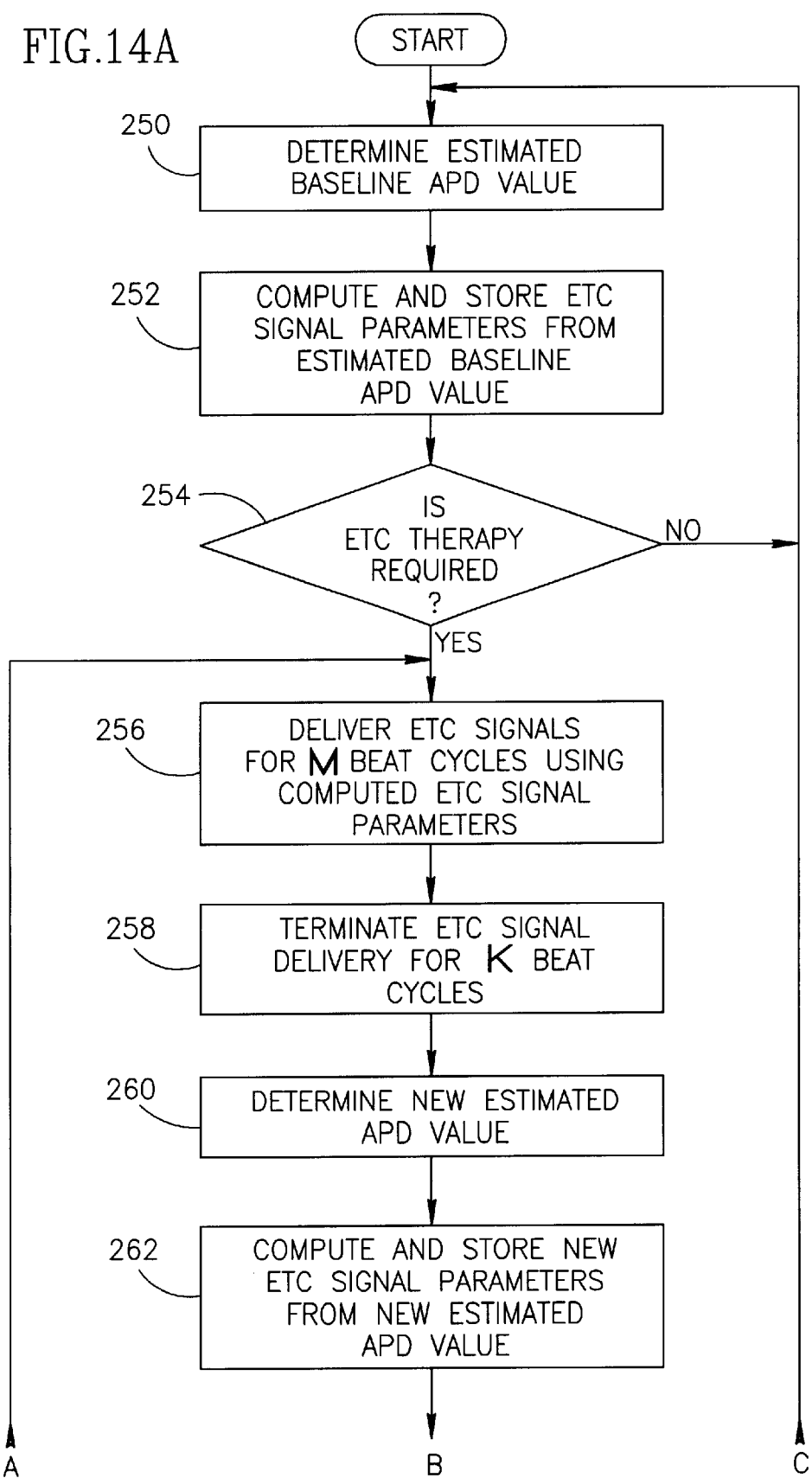
FIGS. 14A and 14B are schematic flow control diagrams illustrating the steps of the method for controlling the ETC signal parameters illustrated in FIGS. 9–13, in accordance within a preferred embodiment of the present invention.
Figure 14B:
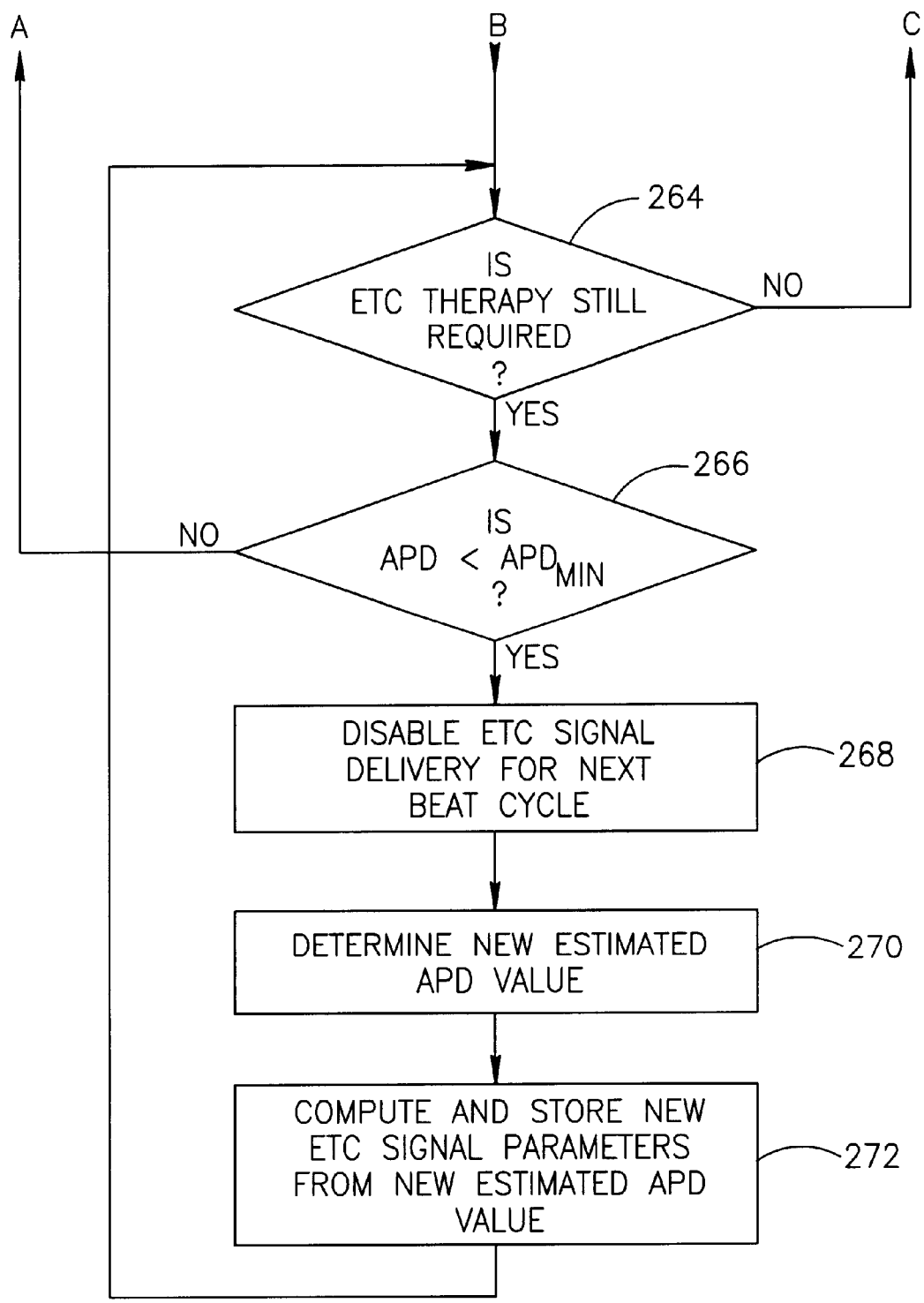

Reference is now made to FIGS. 14A and 14B which are schematic flow control diagrams illustrating the steps of the method for controlling the ETC signal parameters graphically illustrated in FIGS. 9–13, in accordance within a preferred embodiment of the present invention.

The method may be implemented by a program operative on a microprocessor used by the ETC device. The program starts by determining an estimated baseline APD value (step 250). The determining is done during a time in which there are no effects of ETC therapy delivery (such as, but not limited to, the time $T_0$ of FIG. 9). The program then computes and stores the ETC signal parameters from the estimated baseline APD value (step 252). The program then checks whether ETC therapy is required (step 254). If ETC therapy is not required (as may be indicated by the value of a specific flag or by any other suitable method), the program returns control to step 250 and proceeds with determining the estimated APD value of the next beat cycle. The determination of the estimated APD value may be performed on the MAP Signal or a CBE signal by any of the measurement methods disclosed in detail hereinabove.

If ETC therapy is required, the program delivers ETC signals to the heart for M beat cycles using the stored computed ETC signal parameters (step 256). The program then terminates ETC signal delivery for K beat cycles (step 258). The value of K may be in the range of 5–15 beat cycles, but other values outside of this range may also be used, depending on the particular patient and the circumstances.

The program then determines the new estimated APD value in one or more of the K beat cycles during which no ETC delivery is performed (step 260). The program then computes new updated ETC signal parameters from the updated values and stores the updated values (step 262). The program then checks whether ETC therapy is still required (step 264). If ETC therapy is not required, the program returns control to step 250. If ETC therapy is still required, the program checks whether $APD < APD_{MIN}$ (step 266), wherein APD is the current estimated APD value and $APD_{MIN}$ is the minimal acceptable action potential duration value. The value of $APD_{MIN}$ may be a preset safety value which is manually set by a physician based on the physician's empirical determination of the shortest acceptable estimated APD following which an ETC signal may still be safely delivered to the patient's heart without endangering the patient.

If APD is larger than or equal to $APD_{MIN}$, the program returns control to step 256. If $APD < APD_{MIN}$, the program disables the delivery of an ETC signal in the next beat cycle (step 268), determines a new estimated APD value in the next beat cycle, (in which the ETC signal delivery was disabled) (step 270), computes new ETC signal parameters from the new estimated APD value and stores the computed values of the ETC signal parameters (step 272) and returns control to step 264. The steps 264 to 272 are thus repeated until APD is larger than or equal to $APD_{MIN}$ or until ETC therapy is no longer required.

It will be appreciated that, while the methods disclosed hereinabove perform the computation of the ETC signal parameters based on the value of the estimated APD determined in a single beat cycle, other methods may be adapted to provide some form of averaged estimated APD as a basis for the computation of the ETC signal parameters. Since some beat to beat variation of the APD can be expected, such averaging may have the advantage of providing a better APD estimate which may improve the reliability of the computed ETC signal parameters. The averaging may be performed using various averaging methods known in the art, such as, but not limited to, walking average methods including infinite impulse response (IIR) methods and finite impulse response (FIR) methods, with or without distinct weighting. However, other suitable averaging methods may also be used.

For example, in the method of FIG. 8, step 150 may include, in addition to determining the estimated APD value for the current beat cycle, the step (not shown in FIG. 8) of using stored data of the last L beat cycles (including the current beat cycle) for computing a current average estimated APD value using a walking average (also known as a "moving average") method such as a FIR or IIR method with or without weighting, or any other suitable averaging method, wherein L is a relatively small number of contiguous beat cycles. In such a method, step 152 is modified to compute and store updated ETC signal parameters from the current average estimated APD value instead of from the current estimated APD value of the current beat cycle.

Similarly, in the method of FIG. 14, step 250 may include, in addition to determining the estimated baseline APD value for the current beat cycle, the step (not shown in FIG. 14) of using stored data of the last L beat cycles (including the current beat cycle) for computing a current average estimated APD value using a walking average (also known as a "moving average") method such as a FIR or IIR method with or without weighting, or any other suitable averaging method, wherein L is a relatively small number of contiguous beat cycles. In such a method, step 252 is modified to compute and store updated ETC signal parameters from the current average estimated APD value instead of from the current estimated APD value of the current beat cycle. Additionally, in step 260 (FIG. 14), the new estimated APD value may be based on using stored data of the last P beat cycles (including the current beat cycle) for computing a current average estimated APD value using a walking average method such as a FIR or IIR method with or without weighting, or any other suitable averaging method, wherein P is a relatively small number of contiguous beat cycles. In cases where the ETC signal delivery is interrupted solely for the reason of acquiring a signal free of the ETC related artifact, ideally, K=P. However, it is also possible to use values of K and P such that K≠P. After this current average estimated APD value is computed in step 260 it is used to compute the new ETC signal parameters of step 262.

It is noted that, since the methods of the present invention are predictive in the sense that they compute a predicted value of the ETC signal parameters for the next beat cycle or cycles based of an estimated APD value determined from one or more APD values preceding the next beat cycle, it may also be possible to improve the predictive value of the present methods by detecting trends in the previously determined estimated APD values. For example, the method may compute the slope of a linear curve fitted (by using a linear curve fit computation) to a certain specified number of estimated APD values acquired for a specified number of beat cycles, such as, but not limited to, the estimated APD values of the last N beat cycles and stored in a memory unit (not shown). The value of N may be in the range of 5–15 beat cycles, however, other different values of N may also be used depending, inter alia, on the particular patient condition, ETC signal delivery rate and the rate of change of the APD. The method may then use the slope value obtained to compute a predicted value of the APD expected in the next beat cycle and use this predicted APD value for computing one or more of the ETC signal parameters, such as The ETC signal delay, duration, amplitude, shape, polarity or any other desired parameters. Methods for computing such a predicted value based on a slope approximation are well known in the art.

Thus, the methods and devices disclosed hereinabove make use of the MAP or CBE signals to obtain a current estimated APD or a mean estimated APD value based on data measured in a few preceding cardiac beat cycles. This current value or mean value of the estimated APD is used to compute the ETC parameters for applying an ETC signal in a beat cycle immediately following the current beat cycle, based on the assumption that the APD in the following beat cycle will be similar to the APD in the current beat cycle or to the mean APD of the few preceding beat cycles, respectively. Thus, these methods and devices are predictive in nature.

The inventors of the present invention have further noticed that when the MAP or the CBE signal is monitored on a beat by beat basis, the sensed MAP or CBE signal contains information which may be used for automatic termination of the ETC signal in situations in which a premature fast repolarization occurs within the duration of the ETC signal delivered to the heart.

Since effective application of non-excitatory ETC signals involves the delivery of the ETC signals at specific times within the duration of the cardiac action potential, the above disclosed devices and methods have the advantage of providing automatic, dynamic assessment of the APD (or of a parameter proportional thereto) of the locally sensed cardiac action potential, allowing dynamic computation of efficient and effective excitable tissue control signal parameters.

It is noted that while the non-limiting examples of the methods and devices disclosed hereinabove are adapted to compute the delay and duration parameters of the ETC signal, such methods and devices may be suitably adapted to compute additional or different ETC signal parameters such as, but not limited to, the waveform, envelope and polarity of the ETC signal based on the estimated value of the APD obtained in any of the methods disclosed hereinabove.

For example, the lengthening of the estimated APD beyond a certain duration may serve as a trigger to switch to a new or different ETC signal waveform. Such a selecting method may use a look up table (LUT) or data array stored in a memory device (not shown) included in the ETC device which includes data associating a certain ETC parameter with a defined range of APD values. Thus, a program may check the current value of the estimated APD, find out which APD range it falls into, and select from the LUT one or more of the associated ETC parameters to be used in the next beat cycle.

In accordance with another preferred embodiment of the present invention, The LUT may include stored data associating each range of APD values with a set including a plurality of values of the ETC parameters. For example, each range of APD values may be associated with a particular value representing a specific ETC signal waveform and with a specific value of ETC amplitude.

The values of the ETC parameters stored in the LUT and associated with the various APD ranges may be empirically determined for each specific patient in a test period in which patient data is collected under various conditions. In such a test period, the values of the various ETC signal parameters which are safe and optimally efficient may be determined. This test period may be performed under the supervision of a physician, cardiologist, or other expert. The resulting data of the LUT may then be stored and telemetrically or non-telemetrically programmed into the ETC device for automatic operation.

Reference is now made to FIGS. 15A and 15B. FIG. 15A is a schematic diagram illustrating a device for controlling the delivery of excitable tissue control signals to the heart of a patient based on close bipolar electrogram sensing, and for pacing the heart, in accordance with a preferred embodiment of the present invention. FIG. 15B is a schematic diagram illustrating an enlarged view of the lead and electrodes used for close bipolar sensing and for delivering ETC signals, in conjunction with the device illustrated in FIG. 15A.

The ETC device 340 includes an implantable case or housing 341 for housing the circuitry components and the power source 360 of the ETC device 340. The ETC device 40 further includes sense units 342. The sense units 342 of the preferred embodiment of FIG. 15A include a right atrial sense unit 342A, a right ventricle sense unit 342B and a left ventricle sense unit 342C. The sense units 342A, 342B and 342C include circuitry adapted for sensing electrical activity in various cardiac sites and for detecting depolarization events in the signals sensed at these cardiac sites, as is known in the art. The sensing units 342 are operatively connected to electrodes included in a plurality of leads 362, 364 and 366 implanted in the heart 349 of a patient. The sense unit 342A is electrically connected to an electrode 362A included in a lead 362 which is implanted in the right atrium (RA) 352 of the heart 349, the sense unit 342B is electrically connected to an electrode 364A included in a lead 364 which is implanted in the right ventricle (RV) 354 of the heart 349, and the sense unit 342C is electrically connected to a pair of CBE electrodes 370A and 370B included in a lead 366 which is implanted in or about the left ventricle (LV) 356 of the heart 349.

Preferably, the atrial lead 362 is inserted into the right atrium 352 through the sub-clavian vein (not shown) and the superior vena cava (SVC) 363, but other different methods of insertion are also possible. The right ventricular lead 364 is preferably inserted into the RV through the sub-clavian vein (not shown), the SVC 363 and the right atrium 352, but other different methods of insertion are also possible. The lead 366 is preferably inserted through the sub-clavian vein (not shown), passing through the SVC 363, the right atrium 352, the coronary sinus (not shown) and the great cardiac vein (not shown) and reaching a lateral vein (not shown) of the GCV or a branch thereof. In this preferred lead positioning method, the CBE electrodes 370A and 370B are positioned in proximity to the wall of a the lateral vein (not shown) of the GCV. The electrodes 370A and 370B are used for local sensing of left ventricular electrical activity to obtain a CBE signal as disclosed in detail hereinabove. The lead 366 also includes a pair of ETC electrodes 366A and 366B which are used for delivering ETC signals (if required) to the left ventricle 366 through the wall of the lateral vein of the GCV.

The implantable case 341 is typically implanted in a thoracic sub-cutaneous pocket (not shown), but other implantation positions are also possible. It is noted that the above disclosed lead placements and insertion paths and the case placement are given by way of example only and that other electrode placements and lead insertion paths and case placements are also possible.

It is noted that while each of the single electrodes 362A, 364A may be used for sensing with respect to a common reference point such as the case 341 of the ETC device 340, other preferred embodiments of the present invention may use locally applied pairs of electrodes (not shown) which may be used for local differential sensing. For example, the lead 362 may include a pair of electrodes (not shown) which are applied to the right atrium 352 for local differential sensing, the lead 364 may include a pair of electrodes (not shown) which are applied to the right ventricle 354 for local differential sensing. The pair of CBE electrodes 370A and 370B of the lead 366 may be used for CBE sensing in the left ventricle 356.

The ETC device 340 further includes a pacing unit 344, an ETC unit 346 and a microprocessor or controller unit 348. The microprocessor unit 348 is operatively connected to the pacing unit 344 and to the ETC unit 346 for controlling the pacing operation of the pacing unit 344 as is known in the art, and for controlling the operation of the ETC unit 346 as is known in the art and as disclosed in U.S. patent applications Ser. Nos. 09/276,460 and 09/328,068 to Mika et al., (Now U.S. Pat. No. 6,223,072), and in U.S patent application Ser. No. 09/338,649 to Mika et al., filed Jun. 23, 1999, cited hereinabove. The pacing unit 344 may be any suitable pacing unit known in the art and is adapted to controllably deliver pacing pulses to the heart 349. In the preferred embodiment of FIG. 15, the pacing unit 344 is suitably electrically connected to the electrode 362A of the lead 362, for delivering pacing pulses to the right atrium 352 as is known in the art. The pacing unit 344 is also suitably electrically connected to the electrode 364A of the lead 364, for delivering pacing pulses to the right ventricle 354.

It is further noted that while the electrode 362A of the lead 362 is used for both sensing and pacing the RA 352, in other preferred embodiments of the present invention the lead 362 may include additional electrodes or electrode pairs (not shown) such that one or more electrode or electrode pair is used for sensing in the right atrium 352 while other separate electrode(s) or electrode pairs are used for pacing the right atrium 352. Similarly, in accordance with a preferred embodiment of the present invention, the lead 364 may include more than one electrode or pair of electrodes (not shown) which may be separately used for sensing and for pacing the right ventricle 354. Yet similarly, the lead 366 may include more than one electrode pairs (not shown) used for CBE sensing in different locations of the left ventricle 356 and one or more additional ETC electrodes or electrode pairs (not shown) used for delivering non-excitatory ETC signals to different locations the left ventricle 356.

It will therefore be appreciated by those skilled in the art, that the number and arrangement of the electrodes within the leads 362, 364 and 366 may be varied in many ways and many combinations may be used which are all within the scope and spirit of the present invention.

It is further noted that the pacing unit in conjunction with the microprocessor unit 48 may implement pacing of the heart using any suitable pacing modes which are known in the art such as DDD, DDDR, VVI, VDI and VDD modes or any other pacing modes compatible with the delivering of ETC signals to the paced heart.

The ETC device 340 further includes timer unit(s) 345 suitably connected to the microprocessor unit 348, a memory unit 347 suitably connected to the microprocessor unit 348, and a telemetry unit 343 suitably connected to the microprocessor unit 348. The memory unit 345 may include any suitable memory devices known in the art for storing and/or retrieving data by the microprocessor unit 348 suitable for operation in implantable or non-implantable ETC or pacemaker devices.

The telemetry unit 343 may be any suitable telemetry device capable of transmitting data and/or receiving data from a transceiver device (not shown) external to the patient. Such telemetry devices are well known in the art, are not the subject of the present invention and are therefore not described in detail hereinafter.

The timer unit(s) 345 may be any suitable devices adapted to provide clocking signals and to operate as timers for timing the various timing intervals, such as but not limited to the atrio-ventricular interval (AVI interval), ventricular refractory period interval (VRP interval), postventricular atrial refractory period interval (PVARP interval), and any other time intervals known in the art of pacemakers which are required for the operation of the pacing unit 344, in a desired pacing mode and for implementing any of the timing functions required for determining the estimated action potential duration value as disclosed in detail hereinabove. Additionally, the timer unit(s) 345 are adapted to provide the various timing intervals useful for operating the ETC device 340 to deliver ETC signals to the heart. For example, the timer unit(s) 345 may be used to implement any selected ones of the time intervals disclosed in U.S. patent applications Ser. Nos. 09/276,460 and 09/328,068 (now U.S. Pat. No. 6,223,072) to Mika et al. and in U.S. patent application Ser. No. 09/338,649 to Mika et al., filed Jun. 23, 1999, cited hereinabove. Such time intervals may include, the time intervals $\Delta T1$, $\Delta T2$, $\Delta T3$, $\Delta T4$, $\Delta T5$, and $\Delta T7$ which are disclosed in U.S. patent application Ser. No. 09/276,460 to Mika et al.

The device 340 further includes an APD determining unit 350 operatively connected to the CBE electrodes 370A and 370B of the lead 366. The APD determining unit 350 may be implemented using different circuitry configurations as shown in detail hereinabove. For example, in accordance with one preferred embodiment, the APD determining unit 350 may include the CBE sensing unit 33 of FIG. 3B and the APD determining circuit 34 of FIG. 3B, operatively connected as illustrated in FIG. 3B. In this embodiment, the APD determining unit 34 is operatively connected to the microprocessor unit 348 of FIG. 15A. In a non limiting example of this embodiment, the APD determining unit 34 is implemented as the circuitry 40 of FIG. 4. However, other alternative implementations are possible. In operation of such an embodiment, the APD determining unit 350 in conjunction with the microprocessor 348 perform all the functions, including the computational and control functions, disclosed for the APD determining unit 31B of FIG. 3B.

In accordance with another preferred embodiment of the invention, the APD determining unit 350 may include the CBE sensing unit 33 of FIG. 3C and the digitizing unit 39 of FIG. 3C, operatively connected as illustrated in FIG. 3C. In this embodiment, the digitizing unit 39 is operatively connected to the microprocessor unit 348 of FIG. 15A. In operation of such an embodiment, the APD determining unit 350 in conjunction with the microprocessor 348 perform all the functions, including the computational and control functions, disclosed for the APD determining unit 31C of FIG. 3C.

Preferably, the arrangement of the ETC electrodes 366A and 366B and of the CBE electrodes 370A and 370B is as illustrated in FIG. 15. In accordance with this embodiment the ETC electrodes 366A and 366B are spaced apart along the longitudinal axis (not shown) of the lead 366. The pair of CBE electrodes 370A and 370B is disposed between the ETC electrodes 366A and 366B. Preferably, each of the CBE electrodes 370A and 370B has a longitudinal dimension of 1–3 millimeters and the spacing 370C separating the CBE electrode 370A from the CBE electrode 370B along the longitudinal axis of the lead 366 is approximately 1 millimeter.

It is noted that, while these values were empirically found to provide adequate CBE electrogram signals, other sizes and separations of the CBE electrodes 370A and 370B may be used provided that the quality of the sensed CBE signal is adequate for computing the estimated APD value as disclosed in detail hereinabove. Typically, the ETC electrodes 366A and 366B have larger surface areas and larger longitudinal extension along the lead 366 than the corresponding dimensions and extension of the CBE electrodes 370A and 370B. For example, in accordance with one exemplary embodiment of the present invention, each of the ETC electrodes 366A and 366B extends approximately 5–7 millimeters along the longitudinal axis of the lead 366 and are longitudinally separated by a distance of approximately 5–10 millimeters along the lead 66, and the pair of CBE electrodes 370A and 370B are symmetrically disposed with respect to the midline (not shown) between the ETC electrodes 366A and 366B. However, other geometrical sizes and separations of the ETC electrodes are possible and other, including non-symmetrical, positioning methods of the CBE electrodes 370A and 370B relative to the ETC electrodes 366A and 366B are also possible as long as the sensed CBE electrogram signal is adequate for computational purposes and as long as the ETC electrodes enable the delivery of the desired ETC signal parameters to adequately modulate the contractility of the myocardial muscle at or about the region of the delivery of the ETC signal.

Typically, the CBE electrodes 370A and 370B and the ETC electrodes 366A and 366B are constructed by winding a plurality of loops (not shown) of electrically conducting wires made from a bio-compatible material such as platinum or titanium on the electrically isolating external lead sheath (not shown) of the lead 366 as is known in the art, and electrically connecting the wire loops to suitable electrically conducting wires extending inside the lead 366. However, any other suitable method known in the art for constructing the CBE electrodes 370A and 370B and/or the ETC electrodes 366A and 360B may be used.

It is noted that, while the preferred embodiment of FIGS. 15A and 15B uses only a single pair of ETC electrodes 366A and 366B and a single pair of CBE electrodes 370A and 370B, other preferred embodiments may be constructed in which additional pairs (not shown) of CBE electrodes and ETC electrodes are used. Such cases may be useful in clinical applications in which ETC delivery is required at more than one cardiac site.

It is noted that, while in the ETC device 340 of FIG. 15A, the pair of CBE electrodes 370A and 370B are used for local sensing of the LV depolarization event and are shown to be electrically connected to the sense unit 342C, the device 340 may also be implemented such that the APD determining unit 350 is adapted to perform the local sensing using the differential CBE signal, obviating the need for the sense unit 342C. For example, the first component 30A of the CBE signal of FIG. 2B may be used for triggering the ETC signal delivery based on a threshold crossing method or on any other suitable detection method known in the art of sense amplifiers and detection circuits used for detection of a cardiac depolarization wave.

Furthermore, each of the ETC devices 32A–32E and 340 disclosed hereinabove and illustrated in FIGS. 3A–3E and 15A, respectively, may include a sensing electrode (not shown) implanted at or near the cardiac site at which the ETC signals are delivered for sensing a cardiac electrogram signal which is used for detecting the depolarization event representing the arrival of the action potential at or near the cardiac site at which the ETC signals are delivered. This electrode may or may not be included in the lead which includes other electrodes such as the ETC electrodes and the CBE electrodes or MAP electrodes. In accordance with one embodiment of the present invention, the detected depolarization event of this sensing electrode may be used for timing the ETC signal delivery (by starting the counting of the ETC delay period from the time of detection of the depolarization event). However, in accordance with other embodiments of the present invention, in ETC devices having MAP sensing capabilities, such as the ETC devices 32D and 32E (of FIGS. 3D and 3E, respectively) the time of crossing of the threshold value by the sharp leading edge of the MAP signal may be used for timing the ETC signal delivery. Additionally, in accordance with other embodiments of the present invention, in ETC devices having CBE sensing capabilities, such as the ETC devices 32B and 32C (of FIGS. 3B and 3C, respectively) the time of crossing of the threshold value by the first component of the band pass filtered CBE signal may be used for timing the ETC signal delivery.

While the time of these MAP related and CBE related threshold crossings may not be identical to the time of the a detected event based on the sensed cardiac electrogram, the time of these threshold crossings is typically correlated thereto.

Therefore, the time of crossing of the threshold value by the sharp leading edge of the MAP signal and the time of crossing of the threshold value by the first component of the band pass filtered CBE signal may be used for controlling the delivery of the ETC signal.

In accordance with another embodiment of the present invention, the time of crossing of the threshold value by the sharp leading edge of the MAP signal or the time of crossing of the threshold value by the first component of the band pass filtered CBE signal may be used as a safety measure confirming the detection of the sensed depolarization event. For example, the ETC device may enable the delivery of an ETC signal to the heart only if a sensed depolarization event and a crossing of the threshold value by the sharp leading edge of the MAP signal are detected within a predetermined time window defined within a cardiac beat cycle. In another example, the ETC device may enable the delivery of an ETC signal to the heart only if a sensed depolarization event and a crossing of the threshold value by the first component of the band pass filtered CBE signal are detected within a predetermined time window defined within a cardiac beat cycle.

It is noted that, the methods and devices disclosed hereinabove assume that the phases of the action potential within which ETC delivery is effective and safe remain more or less proportional to the duration of the action potential. However, attention should be paid to the fact that the ratio between the duration of the various phases such as the ratio of the effective refractory period and the action potential duration ERP/APD, may change as a function of ETC therapy, the presence of various drugs, heart rate, ischemia, etc. Because of this, a sufficient safety margin is required in the selection of the coefficients $\alpha$, $\beta$, $C_1$ and $C_2$ used in the computation according to the equations 1 and 2 disclosed hereinabove. Furthermore, some of these coefficients may themselves be functions of some of the factors which change the ratios of interest.

It is further noted that, the power sources (internal or external) for energizing some of the devices disclosed hereinabove are not shown in the various drawings. Similarly, except for FIG. 15A, the various memory units, timers, telemetry units and the data busses connecting them with the various microprocessor units of the disclosed devices are not shown. The details of the construction operation and connecting of such power sources, memory units, timers and data busses are well known in the art and are not the subject matter of the present invention.

It will be appreciated by those skilled in the art that, while the methods and devices disclosed hereinabove are adapted to deliver ETC therapy to the left ventricle of the heart, and to determine an estimated APD value in the left ventricle of the heart for controlling the delivery of ETC signals thereto, the present invention may also be adapted to deliver ETC therapy to another cardiac chamber of the heart, and to determine an estimated APD value in that cardiac chamber of the heart. For example, the methods and devices may be adapted to operate on the right ventricle of the heart.

While the invention has been described with respect to a limited number of embodiments, it will be appreciated by the person skilled in the art that many variations, modifications and other applications of the invention may be made.

What is claimed is:

1. A method for automatically controlling the delivery of excitable tissue control signals to a heart of a patient, the method comprising the steps of:

determining an estimated action potential duration value from at least one cardiac action potential related signal sensed at a first cardiac site of said heart;

processing said estimated action potential duration value to obtain at least one excitable tissue control signal parameter; and using said at least one parameter to control the delivery of one or more excitable tissue control signals to a second cardiac site of said heart after the time of occurrence of said at least one cardiac action potential related signal of said step of determining.

2. The method according to claim 1 wherein said at least one cardiac action potential related signal is a close bipolar electrogram signal.

3. The method according to claim 2 wherein said close bipolar electrogram signal includes a first signal component representing the differentiated upstroke of the fast depolarization phase of a cardiac action potential and a second signal component representing the differentiated fast repolarization phase of said cardiac action potential, and wherein said step of determining comprises the steps of:

determining a first time point at which the amplitude of said first signal component first crosses a first threshold value;

determining a second time point at which the amplitude of said second signal component first crosses a second threshold value; and obtaining said estimated action potential duration value by determining the value of the time interval between said second time point and said first time point.

4. The method according to claim 3 wherein said close bipolar electrogram signal also includes a third signal component comprising an electrical artifact induced by the delivery of an excitable tissue control signal to said second cardiac site within the duration of said at least one cardiac action potential and wherein the method further comprises the step of processing said close bipolar electrogram signal to reduce or eliminate said third signal component.

5. The method according to claim 4 wherein said third signal component is reduced or eliminated by using a method selected from signal blanking and active signal canceling.

6. The method according to claim 3 wherein said first threshold value is a positive threshold value and said second threshold value is a negative threshold value.

7. The method according to claim 3 wherein said first threshold value is a negative threshold value and said second threshold value is a positive threshold value.

8. The method according to claim 2 wherein said close bipolar electrogram signal includes a first signal component representing the differentiated upstroke of the fast depolarization phase of a cardiac action potential and a second signal component representing the differentiated fast repolarization phase of said cardiac action potential, and wherein said step of determining comprises the steps of:
   determining a first time point at which the amplitude of said first signal component first crosses a first threshold value going in a first direction;
   determining a second time point at which the amplitude of said second signal component first crosses a second threshold value going in a second direction; and
   obtaining said estimated action potential duration value by determining the value of the time interval between said second time point and said first time point.

9. The method according to claim 8 wherein said first threshold value is a positive threshold value, said first direction is a positive going direction, said second threshold value is a negative threshold value and said second direction is a negative going direction.

10. The method according to claim 8 wherein said first threshold value is a negative threshold value, said first direction is a negative going direction, said second threshold value is a positive threshold value and said second direction is a positive going direction.

11. The method according to claim 1 wherein said first cardiac site is in the vicinity of said second cardiac site.

12. The method according to claim 1 wherein said first cardiac site and said second cardiac site are located in or about the left ventricle of said heart.

13. The method according to claim 1 wherein said at least one cardiac action potential related signal is a monophasic action potential signal.

14. The method according to claim 13 wherein said monophasic action potential signal comprises a sharp leading edge related to the fast depolarization phase of a cardiac action potential and has a maximal amplitude value, and wherein said step of determining comprises the steps of:
   determining a first time point at which the amplitude of said sharp leading edge first crosses a first threshold value;
   determining said maximal amplitude value;
   determining a second time point at which the amplitude value of said monophasic action potential signal is equal to a fraction of said maximal amplitude value; and
   obtaining said estimated action potential duration value by determining the value of the time interval between said second time point and said first time point.

15. The method according to claim 14 wherein said monophasic action potential signal also comprises a artifact component representing an electrical artifact induced by the delivery of an excitable tissue control signal to said second cardiac site within the duration of said at least one cardiac action potential, and wherein the method further comprises the step of processing said monophasic action potential signal to reduce or eliminate said artifact component.

16. The method according to claim 15 wherein said artifact component is reduced or eliminated by using a method selected from signal blanking and active signal canceling.

17. The method according to claim 13 wherein said monophasic action potential signal comprises a sharp leading edge related to the fast depolarization phase of a cardiac action potential and has a maximal amplitude value, and wherein said step of determining comprises the steps of:
   high pass filtering said monophasic action potential signal to obtain a high pass filtered signal;
   processing said high pass filtered signal to determine a first time point at which the amplitude of said high pass filtered signal first crosses a first threshold value;
   low pass filtering said monophasic action potential signal to obtain a low pass filtered signal;
   processing said low pass filtered signal to determine the maximal amplitude value thereof;
   determining a second time point at which the amplitude value of said low pass filtered signal is equal to a fraction of said maximal amplitude value; and
   obtaining said estimated action potential duration value by determining the value of the time interval between said second time point and said first time point.

18. The method according to claim 1 wherein said step of processing comprises computing from said estimated action potential duration value at least one excitable tissue control signal parameter selected from the delay between the detection of a cardiac action potential and the initiation of said excitable tissue control signal, the duration of said excitable tissue control signal, the intensity of said excitable tissue control signal, the waveform of said excitable tissue control signal, the polarity of said excitable tissue control signal and any combination thereof.

19. The method according to claim 18 wherein said at least one excitable tissue control signal parameter is the delay between the detection of a cardiac action potential and the initiation of said excitable tissue control signal and wherein said delay is computed by multiplying said estimated action potential duration value by a first coefficient $\alpha$ to obtain a first computed value, and by adding a first constant $C_1$ to said first computed value.

20. The method according to claim 19 wherein said first coefficient $\alpha$ is in the range of 0.1–0.4.

21. The method according to claim 19 wherein said first coefficient $\alpha$ is empirically determined for said patient.

22. The method according to claim 18 wherein said at least one excitable tissue control signal parameter is the duration of said excitable tissue control signal, and wherein said duration is computed by multiplying said estimated action potential duration value by a second coefficient $\beta$ to obtain a second computed value, and by adding a second constant $C_2$ to said second computed value.

23. The method according to claim 22 wherein said second coefficient $\beta$ is in the range of 0–0.4.

24. The method according to claim 22 wherein said second coefficient $\beta$ is empirically determined for said patient.

25. The method according to claim 1 wherein said at least one cardiac action potential related signal of said step of determining comprises a single cardiac action potential related signal and said estimated action potential duration value is determined based on said single cardiac action potential related signal.

26. The method according to claim 1 wherein said at least one cardiac action potential related signal of said step of determining comprises a plurality of cardiac action potential related signals, and wherein said estimated action potential duration value is determined by computing an average estimated action potential duration from the estimated action potential duration values of each cardiac action potential related signal of said plurality of cardiac action potential related signals.

27. The method according to claim 26 wherein said average estimated action potential duration is computed using a method selected from a weighted moving average method and a non-weighted moving average method.

28. The method according to claim 27 wherein said moving average method is implemented using an implementation method selected from a finite impulse response implementation method and an infinite impulse response implementation method.

29. The method according to claim 1 wherein said first site of said heart is identical to said second site of said heart.

30. The method according to claim 1 further comprising the steps of:
comparing said estimated action potential duration value to a value representing the minimal acceptable action potential duration value; and
disabling the delivery of at least one of said excitable tissue control signals to said second site of said heart if said estimated action potential duration value is smaller than said minimal acceptable action potential duration value.

31. The method according to claim 30 wherein said minimal acceptable action potential duration value is a preset value.

32. The method according to claim 31 further including the step of empirically determining said minimal acceptable action potential duration value for said patient.

33. The method according to claim 31 further including the step of modifying said minimal acceptable action potential duration value based on the results of a checkup procedure performed in said patient.

34. The method according to claim 1 further including the step of providing a look up table including a plurality of action potential duration ranges, each action potential duration range of said plurality of action potential duration ranges is associated with at least one excitable tissue control signal parameter value, wherein said step of processing comprises the steps of,
selecting from said look up table the action potential duration range into which said estimated action potential duration value of said step of determining falls, and
selecting the at least one excitable tissue control signal parameter associated with said action potential duration range as said at least one excitable tissue control signal parameter of said step of processing.

35. Apparatus for automatically controlling the delivery of excitable tissue control signals to a heart of a patient, the apparatus comprising:
means for determining an estimated action potential duration value from at least one cardiac action potential related signal sensed at a first cardiac site of said heart;
means for processing said estimated action potential duration value to obtain at least one excitable tissue control signal parameter; and
means for using said at least one parameter to control the delivery of one or more excitable tissue control signals to a second cardiac site of said heart after the time of occurrence of said at least one cardiac action potential related signal of said step of determining.

36. Apparatus for automatically controlling the delivery of excitable tissue control signals to a heart of a patient, the apparatus comprising:
an excitable tissue control unit for delivering said excitable tissue control signals to a first site of said heart;
an action potential duration determining unit operatively connected to said excitable tissue control unit for receiving action potential related signals sensed at a second site of said heart, determining an estimated action potential duration value from at least one of said action potential related signals, computing at least one excitable tissue control signal parameter and controlling the delivery at least one of said excitable tissue control signals based on said at least one excitable tissue control signal parameter; and
a power source for energizing said excitable tissue control unit and said action potential duration determining unit.

37. The apparatus according to claim 36 further including a case for housing said excitable tissue control unit, said action potential duration determining unit and said power source.

38. The apparatus according to claim 36 further including a pacing unit operatively connected to said action potential duration determining unit and connectable to at least one electrode implanted in said heart for controllably delivering pacing pulses to said heart.

39. The apparatus according to claim 36 further including at least one timing unit operatively connected to said action potential duration determining unit for providing timing signals thereto.

40. The apparatus according to claim 36 further including a memory unit operatively connected to said action potential duration determining unit usable for storing and retrieving data by said action potential duration determining unit.

41. The apparatus according to claim 36 wherein said apparatus is provided with a look up table, stored in said memory unit, said look up table includes a plurality of action potential duration ranges, each action potential duration range of said plurality of action potential duration ranges is associated with at least one excitable tissue control signal parameter value, and wherein said action potential duration determining unit is adapted to select from said look up table the action potential duration range into which said estimated action potential duration value falls, and to select the at least one excitable tissue control signal parameter associated with said action potential duration range as said at least one excitable tissue control signal parameter.

42. The apparatus according to claim 36 wherein said apparatus is an implantable apparatus, and wherein said apparatus further includes a telemetry unit operatively connected to said action potential duration determining unit for communicating with another telemetry unit disposed outside said patient.

43. The apparatus according to claim 36 wherein said action potential duration determining unit comprises:
a close bipolar electrogram sensing unit for sensing close bipolar electrogram signals at said second site of said heart;
a digitizing unit operatively connected to said close bipolar electrogram sensing unit for digitizing said close bipolar electrogram signals sensed by said close bipolar electrogram sensing unit to provide digitized close bipolar electrogram signals; and
a microprocessor unit operatively connected to said digitizing unit and said excitable tissue control unit for receiving said digitized close bipolar electrogram signals, determining an estimated action potential duration value from at least one of said digitized close bipolar electrogram signals, computing at least one excitable tissue control signal parameter from said estimated action potential duration value and controlling the delivery of at least one of said excitable tissue control signals based on said at least one excitable tissue control signal parameter.

44. The apparatus according to claim 43 wherein said closed bipolar electrogram sensing unit comprises a differential amplifier connectable to a pair of electrodes for sensing said close bipolar electrogram signals.

45. The apparatus according to claim 43 wherein said microprocessor is adapted to receive said digitized close bipolar electrogram signal and to obtain therefrom a time value usable as the approximate starting time point of the cardiac action potential corresponding with the currently sensed close bipolar electrogram signal.

46. The apparatus according to claim 43 wherein said close bipolar electrogram signal also comprises an artifact component representing an electrical artifact induced by the delivery of an excitable tissue control signal to said second cardiac site within the duration of sensing said close bipolar electrogram signal, and wherein said microprocessor unit is adapted for processing said close bipolar electrogram signal to reduce or eliminate said artifact component.

47. The apparatus according to claim 43 wherein said at least one excitable tissue control signal parameter computed by said microprocessor unit is selected from the delay between the detection of a cardiac action potential and the initiation of an excitable tissue control signal, the duration of said excitable tissue control signal, the intensity of said excitable tissue control signal, the waveform of said excitable tissue control signal, the polarity of said excitable tissue control signal and any combination thereof.

48. The apparatus according to claim 47 wherein said at least one excitable tissue control signal parameter is the delay between the detection of a cardiac action potential and the initiation of said excitable tissue control signal and wherein said microprocessor unit is adapted for computing said delay by multiplying said estimated action potential duration value by a first coefficient $\alpha$ to obtain a first computed value, and by adding a first constant $C_1$ to said first computed value.

49. The apparatus according to claim 48 wherein said first coefficient $\alpha$ is in the range of 0–0.6.

50. The apparatus according to claim 49 wherein said first coefficient $\alpha$ is empirically determined for said patient.

51. The apparatus according to claim 47 wherein said at least one excitable tissue control signal parameter is the duration of an excitable tissue control signal, and wherein said duration is computed by multiplying said estimated action potential duration value by a second coefficient $\beta$ to obtain a second computed value, and by adding a second constant $C_2$ to said second computed value.

52. The apparatus according to claim 51 wherein said second coefficient $\beta$ is in the range of 0–0.4.

53. The apparatus according to claim 51 wherein said second coefficient $\beta$ is empirically determined for said patient.

54. The apparatus according to claim 43 wherein said at least one of said digitized close bipolar electrogram signals is a single digitized close bipolar electrogram signal and said estimated action potential duration value is determined based on said single digitized close bipolar electrogram signal.

55. The apparatus according to claim 43 wherein said at least at least one of said digitized close bipolar electrogram signals comprises a plurality of digitized close bipolar electrogram signals, and wherein said estimated action potential duration value is determined by computing an average estimated action potential duration from the estimated action potential duration values of each digitized close bipolar electrogram signal of said plurality of digitized close bipolar electrogram signals.

56. The apparatus according to claim 55 wherein said microprocessor is adapted to compute said average estimated action potential duration by using a moving average program selected from a weighted moving average program and a non-weighted moving average program.

57. The apparatus according to claim 56 wherein said moving average program is implemented using an implementation method selected from a finite impulse response implementation method and an infinite impulse response implementation method.

58. The apparatus according to claim 43 wherein said microprocessor unit is adapted to disable the delivery of at least one of said excitable tissue control signals to said second site of said heart if said estimated action potential duration value is smaller than a minimal acceptable action potential duration value.

59. The apparatus according to claim 58 wherein said minimal acceptable action potential duration value is a preset value.

60. The apparatus according to claim 43 further including a memory unit operatively connected to said microprocessor unit, wherein said apparatus is provided with a look up table, stored in said memory unit, said look up table includes a plurality of action potential duration ranges, each action potential duration range of said plurality of action potential duration ranges is associated with at least one excitable tissue control signal parameter value, and wherein said action potential duration determining unit is adapted to select from said look up table the action potential duration range into which said estimated action potential duration value falls, and to select the at least one excitable tissue control signal parameter associated with said action potential duration range as said at least one excitable tissue control signal parameter.

61. The apparatus according to claim 43 wherein said close bipolar electrogram signal includes a first signal component representing the differentiated upstroke of the fast depolarization phase of a cardiac action potential and a second signal component representing the differentiated fast repolarization phase of said cardiac action potential, and wherein said microprocessor unit is adapted to determine a first time point at which the amplitude of said first signal component first crosses a first threshold value, determine a second time point at which the amplitude of said second signal component first crosses a second threshold value, and to obtain said estimated action potential duration value by determining the value of the time interval between said second time point and said first time point.

62. The apparatus according to claim 61 wherein said microprocessor unit is adapted to determine the amplitude value of the extremum point of said first signal component and the amplitude value of the extremum point of said second signal component, and wherein said first threshold value is a fraction of the amplitude value of said extremum point of said first signal component and said second threshold value is a fraction of the amplitude value of said extremum point of said second signal component.

63. The apparatus according to claim 62 wherein said first threshold value is 50% of the amplitude value of said extremum point of said first signal component and said second threshold value is 50% of the amplitude value of said extremum point of said second signal component.

64. The apparatus according to claim 36 wherein said at least one of said action potential related signals comprises at least one cardiac close bipolar electrogram signal, and wherein said action potential duration determining unit comprises:

a close bipolar electrogram sensing unit for sensing close bipolar electrogram signals at said second site of said heart;

an action potential duration determining circuit operatively connected to said close bipolar electrogram sensing unit for receiving said close bipolar electrogram signals, and for processing said close bipolar electrogram signals to provide estimated action potential duration values corresponding to said close bipolar electrogram signals; and a microprocessor unit operatively connected to said action potential duration determining circuit and to said excitable tissue control unit for receiving said estimated action potential duration values, computing at least one excitable tissue control signal parameter from at least one of said estimated action potential duration values and controlling the delivery of at least one of said excitable tissue control signals based on said at least one excitable tissue control signal parameter.

65. The apparatus according to claim 64 wherein said closed bipolar electrogram sensing unit comprises a differential amplifier connectable to a pair of electrodes for sensing said close bipolar electrogram signals.

66. The apparatus according to claim 65 wherein said action potential duration determining circuit comprises:

a first band pass filter operatively connected to the output terminal of said differential amplifier and adapted to preferentially pass a first frequency range corresponding to a first high frequency component of said close bipolar electrogram signals and to produce a first filtered signal;

a second band pass filter operatively connected to the output terminal of said differential amplifier and adapted to preferentially pass a second frequency range corresponding to a second low frequency component of said close bipolar electrogram signals and to produce a second filtered signal;

a first tunable threshold circuit operatively connected to the output terminal of said first band pass filter for generating a first trigger signal when said filtered signal crosses a first threshold value;

a second tunable threshold circuit operatively connected to the output terminal of said second band pass filter for generating a second trigger signal when said second filtered signal crosses a second threshold value; and an edge activated binary counter operatively connected to said first tunable threshold circuit and to said second tunable threshold circuit for receiving and processing said first trigger signal and said second trigger signal to provide an output signal representing an estimated action potential duration value.

67. The apparatus according to claim 66 wherein said first tunable threshold circuit is also operatively connected to said second tunable threshold circuit such that said first trigger signal is fed as a control signal for activating said second tunable threshold circuit.

68. The apparatus according to claim 66 wherein at least one of said first tunable threshold circuit and said second tunable threshold circuit are operatively connected to said microprocessor for receiving control signals therefrom, said signals selected from disabling signals, enabling signals and a combination of disabling signals and enabling signals.

69. The apparatus according to claim 66 wherein said first tunable threshold circuit generates said first trigger signal when said filtered signal crosses a first threshold value going in a first direction, and wherein said second tunable threshold circuit generates said second trigger signal when said second filtered signal crosses a second threshold value going in a second direction.

70. The apparatus according to claim 66 wherein said first threshold value is a positive threshold value and said second threshold is a negative threshold value.

71. The apparatus according to claim 69 wherein said first threshold value is a positive threshold value and said second threshold is a negative threshold value, and wherein said first direction is a positive going direction and said second direction is a negative going direction.

72. The apparatus according to claim 66 wherein said first threshold value is a negative threshold value and said second threshold is a positive threshold value.

73. The apparatus according to claim 69 wherein said first threshold value is a negative threshold value and said second threshold is a positive threshold value, and wherein said first direction is a negative going direction and said second direction is a positive going direction.

74. The apparatus according to claim 66 wherein said microprocessor is adapted to receive said first trigger signal and to obtain therefrom a time value usable as the approximate starting time point of the cardiac action potential corresponding with the currently sensed close bipolar electrogram signal.

75. The apparatus according to claim 66 wherein said first tunable threshold circuit is operatively connected to said second tunable threshold circuit such that said first trigger signal is fed as a control signal for activating said second tunable threshold circuit.

76. The apparatus according to claim 66 wherein said close bipolar electrogram signal also comprises an artifact component representing an electrical artifact induced by the delivery of an excitable tissue control signal to said second cardiac site within the duration of sensing said close bipolar electrogram signal, and wherein said microprocessor unit is adapted for processing said close bipolar electrogram signal to reduce or eliminate said artifact component.

77. The apparatus according to claim 76 wherein said microprocessor unit is operatively connected to said second tunable threshold circuit to provide blanking signals thereto for blanking said artifact component.

78. The apparatus according to claim 66 wherein of said first tunable threshold circuit and said second tunable threshold circuit each include an adjustable threshold setting potentiometer for adjusting the threshold level of said first tunable threshold circuit and said second tunable threshold circuit, respectively.

79. The apparatus according to claim 66 wherein said at least one excitable tissue control signal parameter computed by said microprocessor unit is selected from the delay between the detection of a cardiac action potential and the initiation of an excitable tissue control signal, the duration of said excitable tissue control signal, the intensity of said excitable tissue control signal, the waveform of said excitable tissue control signal, the polarity of said excitable tissue control signal and any combination thereof.

80. The apparatus according to claim 79 wherein said at least one excitable tissue control signal parameter is the delay between the detection of a cardiac action potential and the initiation of said excitable tissue control signal and wherein said microprocessor unit is adapted for computing said delay by multiplying said estimated action potential duration value by a first coefficient $\alpha$ to obtain a first computed value, and by adding a first constant $C_1$ to said first computed value.

81. The apparatus according to claim 80 wherein said first coefficient $\alpha$ is in the range of 0–0.6.

82. The apparatus according to claim 81 wherein said first coefficient α is empirically determined for said patient.

83. The apparatus according to claim 82 wherein said at least one excitable tissue control signal parameter is the duration of an excitable tissue control signal, and wherein said duration is computed by multiplying said estimated action potential duration value by a second coefficient β to obtain a second computed value, and by adding a second constant $C_2$ to said second computed value.

84. The apparatus according to claim 83 wherein said second coefficient β is in the range of 0–0.4.

85. The apparatus according to claim 84 wherein said second coefficient β is empirically determined for said patient.

86. The apparatus according to claim 64 wherein said at least one close bipolar electrogram signal is a single close bipolar electrogram signal and said estimated action potential duration value is determined based on said single one close bipolar electrogram signal.

87. The apparatus according to claim 64 wherein said at least one close bipolar electrogram signal comprises a plurality of close bipolar electrogram signals, and wherein said estimated action potential duration value is determined by computing an average estimated action potential duration from the estimated action potential duration values of each close bipolar electrogram signal of said plurality of close bipolar electrogram signals.

88. The apparatus according to claim 87 wherein said microprocessor is adapted to compute said average estimated action potential duration by using a moving average program selected from a weighted moving average program and a non-weighted moving average program.

89. The apparatus according to claim 88 wherein said moving average program is implemented using an implementation method selected from a finite impulse response implementation method and an infinite impulse response implementation method.

90. The apparatus according to claim 64 wherein said microprocessor unit is adapted to disable the delivery of at least one of said excitable tissue control signals to said second site of said heart if said estimated action potential duration value is smaller than a minimal acceptable action potential duration value.

91. The apparatus according to claim 90 wherein said minimal acceptable action potential duration value is a preset value.

92. The apparatus according to claim 65 further including a memory unit operatively connected to said microprocessor unit, and wherein said apparatus is provided with a look up table, stored in said memory unit, said look up table includes a plurality of action potential duration ranges, each action potential duration range of said plurality of action potential duration ranges is associated with at least one excitable tissue control signal parameter value, and wherein said action potential duration determining unit is adapted to select from said look up table the action potential duration range into which said estimated action potential duration value falls, and to select the at least one excitable tissue control signal parameter associated with said action potential duration range as said at least one excitable tissue control signal parameter.

93. The apparatus according to claim 36 wherein said action potential duration determining unit comprises:

a monophasic action potential sensing unit for sensing monophasic action potential signals at said second site of said heart;

a digitizing unit operatively connected to said monophasic action potential sensing unit for digitizing said monophasic action potential signals sensed by said monophasic action potential sensing unit to provide digitized monophasic action potential signals; and a microprocessor unit operatively connected to said digitizing unit and said excitable tissue control unit for receiving said digitized monophasic action potential signals, determining an estimated action potential duration value from at least one of said digitized monophasic action potential signals, computing at least one excitable tissue control signal parameter from said estimated action potential duration value and controlling the delivery of at least one of said excitable tissue control signals based on said at least one excitable tissue control signal parameter.

94. The apparatus according to claim 93 wherein said microprocessor is adapted to receive said digitized monophasic action potential signal and to obtain therefrom a time value usable as the approximate starting time point of the cardiac action potential corresponding with the currently sensed monophasic action potential signal.

95. The apparatus according to claim 93 wherein said digitized monophasic action potential signal also comprises an artifact component representing an electrical artifact induced by the delivery of an excitable tissue control signal to said second cardiac site within the duration of sensing said monophasic action potential signal, and wherein said microprocessor unit is adapted for processing said digitized monophasic action potential signal to reduce or eliminate said artifact component.

96. The apparatus according to claim 93 wherein said at least one excitable tissue control signal parameter computed by said microprocessor unit is selected from the delay between the detection of a cardiac action potential and the initiation of an excitable tissue control signal, the duration of said excitable tissue control signal, the intensity of said excitable tissue control signal, the waveform of said excitable tissue control signal, the polarity of said excitable tissue control signal and any combination thereof.

97. The apparatus according to claim 96 wherein said at least one excitable tissue control signal parameter is the delay between the detection of a cardiac action potential and the initiation of said excitable tissue control signal and wherein said microprocessor unit is adapted for computing said delay by multiplying said estimated action potential duration value by a first coefficient α to obtain a first computed value, and by adding a first constant $C_1$ to said first computed value.

98. The apparatus according to claim 97 wherein said first coefficient α is in the range of 0–0.6.

99. The apparatus according to claim 97 wherein said first coefficient α is empirically determined for said patient.

100. The apparatus according to claim 96 wherein said at least one excitable tissue control signal parameter is the duration of an excitable tissue control signal, and wherein said duration is computed by multiplying said estimated action potential duration value by a second coefficient β to obtain a second computed value, and by adding a second constant $C_2$ to said second computed value.

101. The apparatus according to claim 100 wherein said second coefficient β is in the range of 0–0.4.

102. The apparatus according to claim 100 wherein said second coefficient β is empirically determined for said patient.

103. The apparatus according to claim 93 wherein said at least one of said digitized monophasic action potential signals is a single digitized monophasic action potential signal and said estimated action potential duration value is determined based on said single digitized monophasic action potential signal.

104. The apparatus according to claim 93 wherein said at least one of said digitized monophasic action potential signals comprises a plurality of digitized monophasic action potential signals, and wherein said estimated action potential duration value is determined by computing an average estimated action potential duration from the estimated action potential duration values of each digitized monophasic action potential signal of said plurality of digitized monophasic action potential signals.

105. The apparatus according to claim 104 wherein said microprocessor is adapted to compute said average estimated action potential duration by using a moving average program selected from a weighted moving average program and a non-weighted moving average program.

106. The apparatus according to claim 105 wherein said moving average program is implemented using an implementation method selected from a finite impulse response implementation method and an infinite impulse response implementation method.

107. The apparatus according to claim 93 wherein said microprocessor unit is adapted to disable the delivery of at least one of said excitable tissue control signals to said second site of said heart if said estimated action potential duration value is smaller than a minimal acceptable action potential duration value.

108. The apparatus according to claim 107 wherein said minimal acceptable action potential duration value is a preset value.

109. The apparatus according to claim 93 further including a memory unit operatively connected to said microprocessor unit, wherein said apparatus is provided with a look up table, stored in said memory unit, said look up table includes a plurality of action potential duration ranges, each action potential duration range of said plurality of action potential duration ranges is associated with at least one excitable tissue control signal parameter value, and wherein said action potential duration determining unit is adapted to select from said look up table the action potential duration range into which said estimated action potential duration value falls, and to select the at least one excitable tissue control signal parameter associated with said action potential duration range as said at least one excitable tissue control signal parameter.

110. The apparatus according to claim 93 wherein said monophasic action potential signal comprises a sharp leading edge related to the fast depolarization phase of a cardiac action potential and has a maximal amplitude value, and wherein said microprocessor unit is adapted to determine a first time point at which the amplitude of said sharp leading edge first crosses a first threshold value, determine said maximal amplitude value, determine a second time point at which the amplitude value of said monophasic action potential signal is equal to a fraction of said maximal amplitude value, and obtain said estimated action potential duration value by determining the value of the time interval between said second time point and said first time point.

111. The apparatus according to claim 110 wherein said second time point is the time point at which said amplitude value of said monophasic action potential signal is equal to 10% of said maximal amplitude value and said estimated action potential duration value is the $MAP_{90}$ value.

112. The apparatus according to claim 36 wherein said at least one of said action potential related signals comprises at least one cardiac monophasic action potential, and wherein said action potential duration determining unit comprises:

a monophasic action potential sensing unit for sensing monophasic action potential signals at said second site of said heart;

an action potential duration determining circuit operatively connected to said monophasic action potential sensing unit for receiving said monophasic action potential signals and processing said monophasic action potential signals to provide estimated action potential duration values corresponding to said monophasic action potential signals; and a microprocessor unit operatively connected to said action potential duration determining circuit and to said excitable tissue control unit for receiving said estimated action potential duration values, computing at least one excitable tissue control signal parameter from at least one of said estimated action potential duration values and controlling the delivery of at least one of said excitable tissue control signals based on said at least one excitable tissue control signal parameter.

113. The apparatus according to claim 112 wherein each of said monophasic action potential signals comprises a leading edge signal component related to the fast repolarization phase of a cardiac action potential and a maximal amplitude value, and wherein said action potential duration determining circuit comprises:

a high pass filter operatively connected to the output terminal of said monophasic action potential sensing unit and adapted to preferentially pass a first frequency range to produce a high pass filtered signal;

a low pass filter operatively connected to the output terminal of said monophasic action potential sensing unit and adapted to preferentially pass a second frequency range to produce a low pass filtered signal;

a first comparator operatively connected to the output terminal of said high pass filter for generating a first trigger signal when said high pass filtered signal crosses a first threshold value;

a peak detector circuit having an input terminal operatively connected to the output terminal of said low pass filter and an output terminal connected to a first potentiometer, for receiving said low pass filtered signal from said low pass filter and for detecting and holding said maximal amplitude value at said output terminal of said peak detector;

a second comparator operatively connected to the output terminal of said low pass filter and to the variable terminal of said potentiometer for generating a second trigger signal when the amplitude of said low pass filtered signal is equal to a fraction of said maximal amplitude value;

an edge activated binary counter operatively connected to said first comparator and to said second comparator for receiving said first trigger signal and said second trigger signal and for providing to said microprocessor unit an output signal representing an estimated action potential duration value.

114. The apparatus according to claim 113 wherein said microprocessor is adapted to receive said first trigger signal and to obtain therefrom a time value usable as the approximate starting time point of the cardiac action potential corresponding with the currently sensed monophasic action potential signal.

115. The apparatus according to claim 113 wherein said first comparator is operatively connected to said second comparator such that said first trigger signal is fed as a control signal for activating said second comparator.

116. The apparatus according to claim 113 wherein said monophasic action potential signal also comprises a artifact component representing an electrical artifact induced by the delivery of an excitable tissue control signal to said second cardiac site within the duration of sensing said monophasic action potential signal, and wherein said microprocessor unit is adapted for processing said monophasic action potential signal to reduce or eliminate said artifact component.

117. The apparatus according to claim 116 wherein said microprocessor unit is operatively connected to at least one of said second comparator and said peak detector to provide blanking signals thereto for reducing or eliminating said artifact component.

118. The apparatus according to claim 113 wherein said peak detector is operatively connected to said microprocessor unit to receive control signals therefrom for resetting said peak detector after said second trigger signal is generated by said second comparator.

119. The apparatus according to claim 113 wherein said fraction of said maximal amplitude value is set by adjusting said potentiometer.

120. The apparatus according to claim 113 wherein said at least one excitable tissue control signal parameter computed by said microprocessor unit is selected from the delay between the detection of a cardiac action potential and the initiation of an excitable tissue control signal, the duration of said excitable tissue control signal, the intensity of said excitable tissue control signal, the waveform of said excitable tissue control signal, the polarity of said excitable tissue control signal and any combination thereof.

121. The apparatus according to claim 120 wherein said at least one excitable tissue control signal parameter is the delay between the detection of a cardiac action potential and the initiation of said excitable tissue control signal and wherein said microprocessor unit is adapted for computing said delay by multiplying said estimated action potential duration value by a first coefficient $\alpha$ to obtain a first computed value, and by adding a first constant $C_1$ to said first computed value.

122. The apparatus according to claim 121 wherein said first coefficient $\alpha$ is in the range of 0–0.6.

123. The apparatus according to claim 122 wherein said first coefficient $\alpha$ is empirically determined for said patient.

124. The apparatus according to claim 120 wherein said at least one excitable tissue control signal parameter is the duration of an excitable tissue control signal, and wherein said duration is computed by multiplying said estimated action potential duration value by a second coefficient $\beta$ to obtain a second computed value, and by adding a second constant $C_2$ to said second computed value.

125. The apparatus according to claim 124 wherein said second coefficient $\beta$ is in the range of 0–0.4.

126. The apparatus according to claim 124 wherein said second coefficient $\beta$ is empirically determined for said patient.

127. The apparatus according to claim 124 wherein said at least one monophasic action potential is a single monophasic action potential and said estimated action potential duration value is determined based on said single monophasic action potential.

128. The apparatus according to claim 112 wherein said at least one monophasic action potential comprises a plurality of monophasic action potentials, and wherein said estimated action potential duration value is determined by computing an average estimated action potential duration from the estimated action potential duration values of each monophasic action potential of said plurality of monophasic action potentials.

129. The apparatus according to claim 128 wherein said microprocessor is adapted to compute said average estimated action potential duration by using a moving average program selected from a weighted moving average program and a non-weighted moving average program.

130. The apparatus according to claim 129 wherein said moving average program is implemented using an implementation method selected from a finite impulse response implementation method and an infinite impulse response implementation method.

131. The apparatus according to claim 112 wherein said microprocessor unit is adapted to disable the delivery of at least one of said excitable tissue control signals to said second site of said heart if said estimated action potential duration value is smaller than a minimal acceptable action potential duration value.

132. The apparatus according to claim 131 wherein said minimal acceptable action potential duration value is a preset value.

133. The apparatus according to claim 113 further including a memory unit operatively connected to said microprocessor unit, and wherein said apparatus is provided with a look up table, stored in said memory unit, said look up table includes a plurality of action potential duration ranges, each action potential duration range of said plurality of action potential duration ranges is associated with at least one excitable tissue control signal parameter value, and wherein said action potential duration determining unit is adapted to select from said look up table the action potential duration range into which said estimated action potential duration value falls, and to select the at least one excitable tissue control signal parameter associated with said action potential duration range as said at least one excitable tissue control signal parameter.

* * * * *

UNITED STATES PATENT AND TRADEMARK OFFICE
CERTIFICATE OF CORRECTION

PATENT NO.  : 6,360,126 B1
DATED       : March 19, 2002
INVENTOR(S) : Yuval Mika et al.

It is certified that error appears in the above-identified patent and that said Letters Patent is hereby corrected as shown below:

Column 40,
Line 38, "0.1-0.4" should be replaced with -- 0-0.6 --.

Column 42,
Line 28, "36" should be replaced with -- 40 --.

Column 43,
Line 6, -- unit -- should be added after the word "microprocessor".

Column 44,
Line 2, -- unit -- should be added after the word "microprocessor".

Column 45,
Line 61, -- unit -- should be added after the word "microprocessor".

Column 46,
Lines 6, 9, 14 and 17, -- value -- should be added after the word "threshold".
Line 20, -- unit -- should be added after the word "microprocessor".

Column 47,
Line 28, -- unit -- should be added after the word "microprocessor".

Column 48,
Line 16, -- unit -- should be added after the word "microprocessor".

Column 50,
Line 59, -- unit -- should be added after the word "microprocessor".

UNITED STATES PATENT AND TRADEMARK OFFICE
CERTIFICATE OF CORRECTION

PATENT NO. : 6,360,126 B1
DATED : March 19, 2002
INVENTOR(S) : Yuval Mika et al.

It is certified that error appears in the above-identified patent and that said Letters Patent is hereby corrected as shown below:

<u>Column 52,</u>
Line 18, -- unit -- should be added after the word "microprocessor".

Signed and Sealed this

Seventeenth Day of February, 2004

JON W. DUDAS
*Acting Director of the United States Patent and Trademark Office*